United States Patent
Lange et al.

(10) Patent No.: US 10,942,183 B2
(45) Date of Patent: Mar. 9, 2021

(54) METHODS OF DETECTING PROGESTERONE RECEPTOR AND OF DETECTING AN EXPRESSION LEVEL

(71) Applicant: REGENTS OF THE UNIVERSITY OF MINNESOTA, Minneapolis, MN (US)

(72) Inventors: Carol Ann Lange, Minneapolis, MN (US); Todd P. Knutson, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 15/945,901

(22) Filed: Apr. 5, 2018

(65) Prior Publication Data

US 2018/0292409 A1 Oct. 11, 2018

Related U.S. Application Data

(60) Provisional application No. 62/481,966, filed on Apr. 5, 2017, provisional application No. 62/500,694, filed on May 3, 2017.

(51) Int. Cl.
| | | |
|---|---|---|
| *A61K 31/56* | (2006.01) | |
| *G01N 33/574* | (2006.01) | |
| *A61K 31/575* | (2006.01) | |
| *A61K 31/567* | (2006.01) | |
| *C12Q 1/6886* | (2018.01) | |

(52) U.S. Cl.
CPC ..... *G01N 33/57415* (2013.01); *A61K 31/567* (2013.01); *A61K 31/575* (2013.01); *C12Q 1/6886* (2013.01); *C12Q 2600/158* (2013.01); *G01N 2333/723* (2013.01); *G01N 2440/14* (2013.01); *G01N 2800/52* (2013.01)

(58) Field of Classification Search
CPC .................................................. A61K 31/575
USPC ......................................................... 514/179
See application file for complete search history.

(56) References Cited

U.S. PATENT DOCUMENTS

2013/0316992 A1   11/2013   Lange

OTHER PUBLICATIONS

Novus Biological "IHC vs ICC vs IF—Do you know the difference?," https://www.novusbio.com/antibody-news/antibodies/ihc-vs-icc-vs-if-do-you-know-the-difference Jan. 30, 2017 (Year: 2017).*
Katkam, "Onapristone (ZK 98.299): a potential antiprogestin for endometrial contraception" 1995 *Am J Obstet Gynecol.*, 173(3 Pt 1):779-87.
Arendt, "Form and function: how estrogen and progesterone regulate the mammary epithelial hierarchy" 2015 *Journal of Mammary Gland Biology and Neoplasia*, 20:9-25.
Asselin-Labat, "Control of mammary stem cell function by steroid hormone signalling" 2010 *Nature*, 465:798-802 (includes 1 page Supplementary Information).

(Continued)

*Primary Examiner* — Shengjun Wang
(74) *Attorney, Agent, or Firm* — Mueting Raasch Group

(57) ABSTRACT

A method that includes testing for the presence of a phosphorylated Ser294 (phospho-Ser294) progesterone receptor (PR). A method that includes determining the expression level of a gene in a patient sample and comparing it to a control sample.

10 Claims, 21 Drawing Sheets
(20 of 21 Drawing Sheet(s) Filed in Color)
Specification includes a Sequence Listing.

(56) References Cited

OTHER PUBLICATIONS

Ballaré, "Two domains of the progesterone receptor interact with the estrogen receptor and are required for progesterone activation of the c-Src/Erk pathway in mammalian cells" 2003 *Mol. Cell. Biol.*, 23:1994-2008.
Banerji, "Sequence analysis of mutations and translocations across breast cancer subtypes" 2012 *Nature*, 486:405-409.
Baniwal, "Runx2 controls a feed-forward loop between androgen and prolactin-induced protein (PIP) in stimulating T47D cell proliferation" 2012 *J. Cell. Physiol.*, 227:2276-2282.
Beleut, "Two distinct mechanisms underlie progesterone-induced proliferation in the mammary gland" 2010 *Proc. Natl. Acad. Sci. USA*, 107(7):2989-2994.
Benjamini, "Controlling the False Discovery Rate: A Practical and Powerful Approach to Multiple Testing" 1995 *J. Royal Statistical Society, Series B*, 57:289-300.
Bentzon, "Prognostic effect of estrogen receptor status across age in primary breast cancer" 2008 *International Journal of Cancer*, 122:1089-1094.
Bolstad, "preprocessCore: A collection of pre-processing functions," package version 1.30.0. (20 pages).
Brisken, "A paracrine role for the epithelial progesterone receptor in mammary gland development" 1998 *Proc. Natl. Acad. Sci. USA*, 95:5076-5081.
Brisken, "Essential function of Wnt-4 in mammary gland development downstream of progesterone signaling" 2000 *Genes Dev.*, 14:650-654.
Brisken, "Progesterone signalling in breast cancer: a neglected hormone coming into the limelight" 2013 *Nat. Rev. Cancer*, 13:385-396.
Brunet, "Metagenes and molecular pattern discovery using matrix factorization" 2004 *Proc. Natl. Acad. Sci. USA*, 101:4164-4169.
Campbell, "Quantitative oestradiol receptor values in primary breast cancer and response of metastases to endocrine therapy" 1981 *Lancet*, 2:1317-1319.
Cancer Genome Atlas Network: Comprehensive molecular portraits of human breast tumours 2012 *Nature*, 490:61-70.
Casado, "The Aryl Hydrocarbon Receptor Relays Metabolic Signals to Promote Cellular Regeneration" 2016 *Stem Cells Int.*, 2016:4389802 (published online Aug. 3, 2016).
Chimge, "The RUNX family in breast cancer: relationships with estrogen signaling" 2013 *Oncogene*, 32:2121-2130.
Ciriello, "Comprehensive Molecular Portraits of Invasive Lobular Breast Cancer" 2015 *Cell*, 163:506-519.
Ciupek, "Androgen receptor promotes tamoxifen agonist activity by activation of EGFR in ERalpha-positive breast cancer" 2015 *Breast Cancer Res. Treat*, 154:225-237.
Clarke, "Non-overlapping progesterone receptor cistromes contribute to cell-specific transcriptional outcomes" 2012 *PLoS One*, 7:e35859 (14 pages).
Clemm, "Differential hormone-dependent phosphorylation of progesterone receptor A and B forms revealed by a phosphoserine site-specific monoclonal antibody" 2000 *Mol. Endocrinol*, 14:52-65.
Cochrane, "Role of the androgen receptor in breast cancer and preclinical analysis of enzalutamide" 2014 *Breast Cancer Res.*, 16:R7.
Curtis, "The genomic and transcriptomic architecture of 2,000 breast tumours reveals novel subgroups." 2012 *Nature*, 486(7403):346-52.
Daniel, "Linkage of progestin and epidermal growth factor signaling: Phosphorylation of progesterone receptors mediates transcriptional hypersensitivity and increased ligand-independent breast cancer cell growth" 2007 *Steroids*, 72:188-201.
Daniel, "Phosphorylation-dependent antagonism of sumoylation derepresses progesterone receptor action in breast cancer cells" 2007 *Mol. Endocrinol.*, 21:2890-2906.
Daniel, "Protein kinases mediate ligand-independent derepression of sumoylated progesterone receptors in breast cancer cells" 2009 *Proc. Natl. Acad. Sci. USA*, 106:14287-14292.
Daniel, "Progesterone receptor-B enhances estrogen responsiveness of breast cancer cells via scaffolding PELP1- and estrogen receptor-containing transcription complexes" 2015 *Oncogene*, 34:506-515.
Davies, "The Androgen Receptor Bridges Stem Cell-Associated Signaling Nodes in Prostate Stem Cells" 2016 *Stem Cells Int.*, 2016:4829602 (published online Jan. 10, 2016).
De Amicis, Androgen receptor overexpression induces tamoxifen resistance in human breast cancer cells. *Breast Cancer Res. Treat.*, 2010, 121:1-11.
Dean, "Therapeutic response to CDK4/6 inhibition in breast cancer defined by ex vivo analyses of human tumors" 2012 *Cell Cycle*, 11:2756-2761.
Diaz-Flaque, "Progesterone receptor assembly of a transcriptional complex along with activator protein 1, signal transducer and activator of transcription 3 and ErbB-2 governs breast cancer growth and predicts response to endocrine therapy" 2013 *Breast Cancer Res.*, 15:R118 (24 pages).
Diep, "Progesterone action in breast, uterine, and ovarian cancers" 2015 *Journal of Molecular Endocrinology*, 54:R31-R53.
Diep, "Active FOXO1 Is a Key Determinant of Isoform-Specific Progesterone Receptor Transactivation and Senescence Programming" 2016 *Mol. Cancer Res.*, 14:141-162 (published online Nov. 17, 2015).
Dressing, "Progesterone receptors act as sensors for mitogenic protein kinases in breast cancer models" 2009 *Endocr. Relat. Cancer*, 16(2):351-361.
Dressing, "Progesterone receptor-cyclin D1 complexes induce cell cycle-dependent transcriptional programs in breast cancer cells" 2014 *Mol. Endocrinol.*, 28:422-457.
Du, lumi: a pipeline for processing Illumina microarray. *Bioinformatics* 2008, 24:1547-1548.
Elbi, "Recruitment of dioxin receptor to active transcription sites" 2002 *Mol. Biol. Cell*, 13:2001-2015.
Elizalde, "ErbB-2 nuclear function in breast cancer growth, metastasis and resistance to therapy" 2016 *Endocr. Relat. Cancer*, 23:T243-T257.
Ferrari, "RUNX2 in mammary gland development and breast cancer" 2013 *J. Cell. Physiol.*, 228:1137-1142.
Gao, "Improving molecular cancer class discovery through sparse non-negative matrix factorization" 2005 *Bioinformatics*, 21:3970-3975.
Gaujoux, A flexible R package for nonnegative matrix factorization. 2010 *BMC Bioinformatics*, 11:367 (9 pages).
Gentleman, J: Bioconductor: open software development for computational biology and bioinformatics. 2004 *Genome Biol.* 5:R80 (16 pages).
Goulding, "A new immunohistochemical antibody for the assessment of estrogen receptor status on routine formalin-fixed tissue samples" 1995 *Hum Pathol.*, 26:291-294.
Graham, "DNA replication licensing and progenitor numbers are increased by progesterone in normal human breast" 2009 *Endocrinology*, 150:3318-3326.
Grimshaw, "Mammosphere culture of metastatic breast cancer cells enriches for tumorigenic breast cancer cells" 2008 *Breast Cancer Res.*, 10:R52 (10 pages).
Hagan, "ck2-dependent phosphorylation of progesterone receptors (PR) on Ser81 regulates PR-B isoform-specific target gene expression in breast cancer cells" 2011 *Mol Cell Biol.*, 31:2439-2452.
Hagan, "Role of phosphorylation in progesterone receptor signaling and specificity" 2012 *Mol Cell Endocrinol.*, 357:43-49.
Hagan, "A Common Docking Domain in Progesterone Receptor-B links DUSP6 and CK2 signaling to proliferative transcriptional programs in breast cancer cells" 2013 *Nucleic Acids Res.*, 41(19):8926-42.
Hilton, "Progesterone and estrogen receptors segregate into different cell subpopulations in the normal human breast" 2012 *Mol. Cell. Endocrinol.*, 361:191-201.
Hosseini, "Early dissemination seeds metastasis in breast cancer" 2016 *Nature*, 540:552-558 (published online Dec. 14, 2016).

(56) References Cited

OTHER PUBLICATIONS

Iacopetta, "The Role of Androgen Receptor in Breast Cancer" 2012 *Drug Discovery Today Disease Mechanisms*, 9:e19-e27.
Ingle, "A double-blind trial of tamoxifen plus prednisolone versus tamoxifen plus placebo in postmenopausal women with metastatic breast cancer: A collaborative trial of the North Central Cancer Treatment Group and Mayo Clinic" 1991 *Cancer*, 68:34-39.
Jaiyesimi, "Use of tamoxifen for breast cancer: twenty-eight years later" 1995 *Journal of Clinical Oncology*, 13:513-529.
Jonat, "Randomized phase II study of lonaprisan as second-line therapy for progesterone receptor-positive breast cancer" 2013 *Annals of Oncology*, 24(10):2543-2548.
Joshi, "Progesterone induces adult mammary stem cell expansion" 2010 *Nature*, 465:803-807.
Kataoka, "Ecotropic viral integration site 1, stem cell self-renewal and leukemogenesis" 2012 *Cancer Sci.*, 103:1371-1377.
Kim, "Sparse non-negative matrix factorizations via alternating non-negativity-constrained least squares for microarray data analysis" 2007 *Bioinformatics*, 23:1495-1502.
Knutson, "Phosphorylated and sumoylation-deficient progesterone receptors drive proliferative gene signatures during breast cancer progression" 2012 *Breast Cancer Res.*, 2012, 14:R95 (23 pages).
Knutson, "Dynamic Regulation of Steroid Hormone Receptor Transcriptional Activity by Reversible SUMOylation" 2013 *Vitam. Horm.*, 93:227-261.
Knutson, "Tracking progesterone receptor-mediated actions in breast cancer" 2014 *Pharmacol. Ther.*, 142:114-125.
Knutson, "Posttranslationally modified progesterone receptors direct ligand-specific expression of breast cancer stem cell-associated gene programs" 2017 *J. Hematol. Oncol.*, 10:89 (published online Apr. 17, 2017).
Lange, "Phosphorylation of human progesterone receptors at serine-294 by mitogen-activated protein kinase signals their degradation by the 26S proteasome" 2000 *Proc. Natl. Acad. Sci. USA*, 97:1032-1037.
Lee, "Learning the parts of objects by non-negative matrix factorization" 1999 *Nature*, 401:788-791.
Li, "PAX Genes in Cancer; Friends or Foes?" 2012 *Front. Genet.*, 3:6 (7 pages).
Lippman, "Quantitative estrogen receptor analyses: the response to endocrine and cytotoxic chemotherapy in human breast cancer and the disease-free interval" 1980 *Cancer*, 46:2829-2834.
Lydon, "Mice lacking progesterone receptor exhibit pleiotropic reproductive abnormalities" 1995 *Genes Dev.*, 9:2266-2278.
McCarty, "Estrogen receptor analyses. Correlation of biochemical and immunohistochemical methods using monoclonal antireceptor antibodies" 1985 *Arch Pathol. Lab. Med.*, 109:716-721.
McDonald, "RUNX2 correlates with subtype-specific breast cancer in a human tissue microarray, and ectopic expression of Runx2 perturbs differentiation in the mouse mammary gland" 2014 *Dis. Model Mech.*, 7:525-534.
Mohammed, "Progesterone receptor modulates ERα action in breast cancer" 2015 *Nature*, 523:313-317.
Moore, "Cyclin dependent kinase 2 and the regulation of human progesterone receptor activity" 2007 *Steroids* 72(2):202-209.
Mootha, "PGC-1α-responsive genes involved in oxidative phosphorylation are coordinately downregulated in human diabetes" 2003 *Nat. Genet.*, 34:267-273.
Narayanan, "Cyclin-dependent kinase activity is required for progesterone receptor function: novel role for Cyclin A/Cdk2 as a progesterone receptor coactivator" 2005 *Mol. Cell. Biol.*, 25:264-277.
Obr, "The biology of progesterone receptor in the normal mammary gland and in breast cancer." 2012 *Mol. Cell. Endocrinol.*, 357:4-17.
Obr, "Progesterone receptor and Stat5 signaling cross talk through RANKL in mammary epithelial cells" 2013 *Mol. Endocrinol.*, 27:1808-1824.
Ohtake, "Cross-talk of dioxin and estrogen receptor signals through the ubiquitin system" 2011 *J. Steroid Biochem. Mol. Biol.*, 127:102-107.

Owens, "Runx2 is a novel regulator of mammary epithelial cell fate in development and breast cancer" 2014 *Cancer Res.*, 74:5277-5286.
Paridaens, "Clinical significance of the quantitative assessment of estrogen receptors in advanced breast cancer" 1980 *Cancer*, 46:2889-2895.
Pierson-Mullany, "Phosphorylation of progesterone receptor serine 400 mediates ligand-independent transcriptional activity in response to activation of cyclin-dependent protein kinase 2" 2004 *Mol. Cell. Biol.*, 24:10542-10557.
Pocar, "Molecular interactions of the aryl hydrocarbon receptor and its biological and toxicological relevance for reproduction" 2005 *Reproduction*, 129:379-389.
Prat, "Prognostic significance of progesterone receptor-positive tumor cells within immunohistochemically defined luminal A breast cancer" 2013 *Journal of Clinical Oncology*, 31:203-209.
Proietti, "Heregulin Co-opts PR Transcriptional Action Via Stat3 Role as a Coregulator to Drive Cancer Growth" 2015 *Mol. Endocrinol.*, 29:1468-1485.
Qiu, "MAP kinases couple multiple functions of human progesterone receptors: degradation, transcriptional synergy, and nuclear association" 2003 *J. Steroid Biochem. Mol. Biol.*, 85:147-157.
Qiu, "Mitogen-activated protein kinase regulates nuclear association of human progesterone receptors" 2003 *Mol. Endocrinol.*, 17:628-642.
Ravindranathan, "Peptidomimetic targeting of critical androgen receptor-coregulator interactions in prostate cancer" 2013 *Nature Communications*, 4:1923 (11 pages).
Ring, "Mechanisms of tamoxifen resistance" 2004 *Endocrine-Related Cancer*, 11:643-658.
Robertson, "Onapristone, a progesterone receptor antagonist, as first-line therapy in primary breast cancer" 1999 *Eur. J. Cancer*, 35:214-218.
Schramek, "Osteoclast differentiation factor RANKL controls development of progestin-driven mammary cancer" 2010 *Nature*, 468:98-102.
Shah, "The clonal and mutational evolution spectrum of primary triple-negative breast cancers" 2012 *Nature*, 486:395-399.
Shen, "Transcriptional hyperactivity of human progesterone receptors is coupled to their ligand-dependent down-regulation by mitogen-activated protein kinase-dependent phosphorylation of serine 294" 2001 *Mol. Cell. Biol.*, 21:6122-6131.
Siegel, "Cancer statistics, 2016" 2016 *CA Cancer J. Clin.*, 66:7-30.
Silberstein, "Expression of the PAX2 oncogene in human breast cancer and its role in progesterone-dependent mammary growth" 2002 *Oncogene*, 21:1009-1016.
Singhal, "Genomic agonism and phenotypic antagonism between estrogen and progesterone receptors in breast cancer" 2016 *Sci. Adv.*, 2:e1501924 (14 pages).
Smyth, "Limma: linear models for microarray data" in: *Bioinformatics and computational biology solutions using R and Bioconductor.* Springer; 2005: 397-420. Cover page, publishers page, table of contents, and Chapter.
Stanford, "Role for the Aryl Hydrocarbon Receptor and Diverse Ligands in Oral Squamous Cell Carcinoma Migration and Tumorigenesis" 2016 *Mol. Cancer. Res.* 14(8):696-706.
Stanford, "The role of the aryl hydrocarbon receptor in the development of cells with the molecular and functional characteristics of cancer stem-like cells" 2016 *BMC Biol.*, 14:20.
Stephens, "The landscape of cancer genes and mutational processes in breast cancer" 2012 *Nature*, 486:400-404.
Stewart, "Estrogen and progesterone receptors: correlation of response rates, site and timing of receptor analysis" 1982 *Breast Cancer Res. Treat.*, 2:243-250.
Subramanian, "Gene set enrichment analysis: a knowledge-based approach for interpreting genome-wide expression profiles" 2005 *Proc. Natl. Acad. Sci. USA*, 102:15545-15550.
Tang, "A Comprehensive View of Nuclear Receptor Cancer Cistromes" 2011 *Cancer Res.*, 71(22):6940-7.
Tanos, "Progesterone/RANKL is a major regulatory axis in the human breast" 2013 *Science Translational Medicine*, 5:182ra155 (10 pages).

(56) References Cited

OTHER PUBLICATIONS

Visvader, "Mammary stem cells and the differentiation hierarchy: current status and perspectives" 2014 *Genes Dev.*, 28:1143-1158.
Weigel, "Steroid receptor phosphorylation: a key modulator of multiple receptor functions" 2007 *Mol. Endocrinol*, 21:2311-2319.
Xu, "A: ESCAPE: database for integrating high-content published data collected from human and mouse embryonic stem cells" 2013 *Database (Oxford)*, 2013:bat045 (12 pages).

* cited by examiner

FIG. 3C Total ER Ab
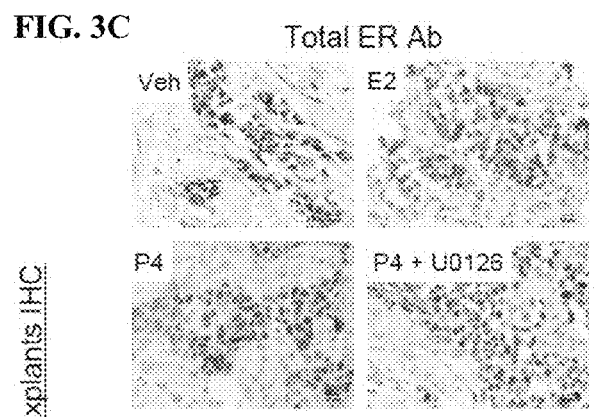
FIG. 3D Total PR Ab
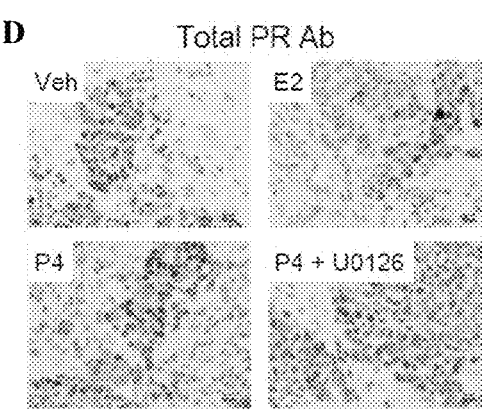
FIG. 3E p294-PR Ab
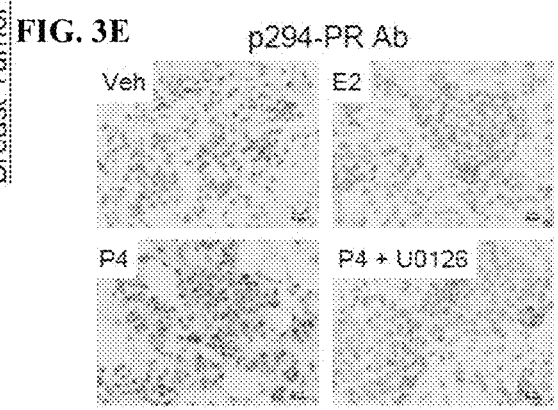
FIG. 3F pERK1/2 Ab
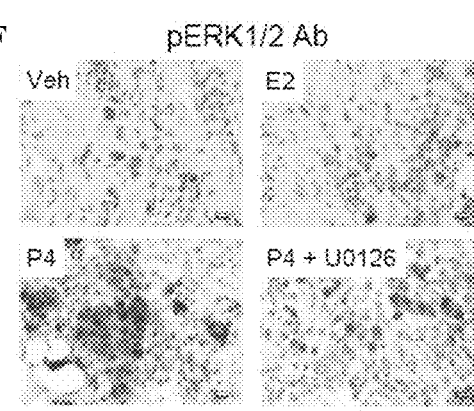

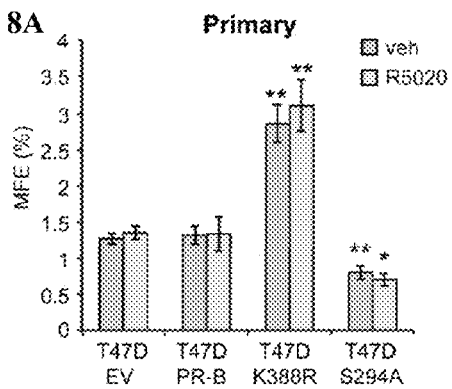
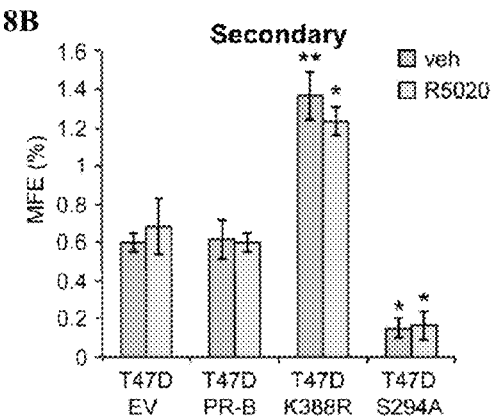
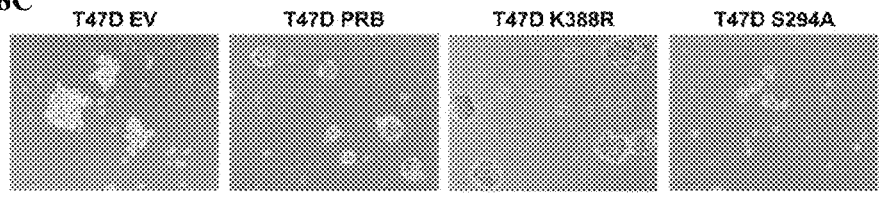
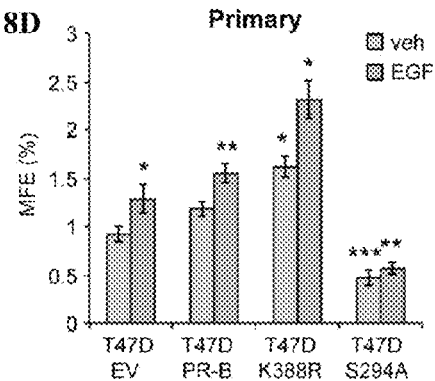
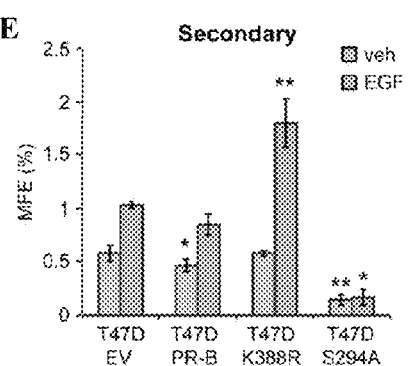
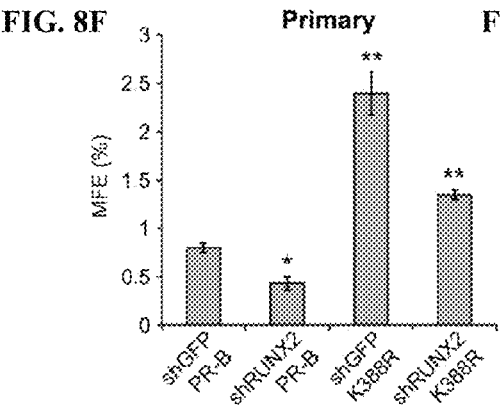
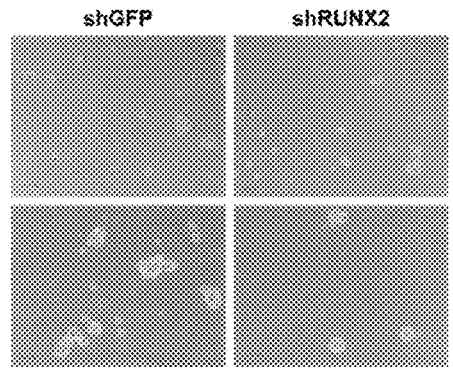

SEQUENCE LISTING

<160> NUMBER OF SEQ ID NOS: 17

<210> SEQ ID NO 1

<211> LENGTH: 50
<212> TYPE: DNA
<213> ORGANISM: artificial
<220> FEATURE:
<223> OTHER INFORMATION: probe sequence
<400> SEQUENCE: 1
ctgaggcaag ccatggagtg agacccagga gccggacact tctcaggaaa    50

<210> SEQ ID NO 2
<211> LENGTH: 50
<212> TYPE: DNA
<213> ORGANISM: artificial
<220> FEATURE:
<223> OTHER INFORMATION: probe sequence
<400> SEQUENCE: 2
gcccttcacc attgtggaat gatgccctgg ctttaaggtt tagctccaca    50

<210> SEQ ID NO 3
<211> LENGTH: 50
<212> TYPE: DNA
<213> ORGANISM: artificial
<220> FEATURE:
<223> OTHER INFORMATION: probe sequence
<400> SEQUENCE: 3
gcagactgcc ccaatgtgac agcacctgtt tgtgcctcaa atggccacac    50

<210> SEQ ID NO 4
<211> LENGTH: 50
<212> TYPE: DNA
<213> ORGANISM: artificial
<220> FEATURE:
<223> OTHER INFORMATION: probe sequence
<400> SEQUENCE: 4
aacagtctct ccgccccgca ccagatcaag tagtttggac atcaccctac    50

<210> SEQ ID NO 5
<211> LENGTH: 50
<212> TYPE: DNA
<213> ORGANISM: artificial
<220> FEATURE:
<223> OTHER INFORMATION: probe sequence
<400> SEQUENCE: 5
cccaagcaag ccagtgagca gccctgccag actactgcca gactgagaaa    50

<210> SEQ ID NO 6
<211> LENGTH: 50
<212> TYPE: DNA
<213> ORGANISM: artificial
<220> FEATURE:
<223> OTHER INFORMATION: probe sequence
<400> SEQUENCE: 6
tccctgatat acaccatccc caattgctcc ttctcacctc ctctcaggcc    50

<210> SEQ ID NO 7
<211> LENGTH: 50
<212> TYPE: DNA
<213> ORGANISM: artificial
<220> FEATURE:
<223> OTHER INFORMATION: probe sequence
<400> SEQUENCE: 7
gagtcgtgat tgtaccactg cattcctgct gagcaacaga gtgagacccc                              50

<210> SEQ ID NO 8
<211> LENGTH: 50
<212> TYPE: DNA
<213> ORGANISM: artificial
<220> FEATURE:
<223> OTHER INFORMATION: probe sequence

<400> SEQUENCE: 8
cagaagtcct agacagtgac atttcttaat ggtgggagtc cagctcatgc                              50

<210> SEQ ID NO 9
<211> LENGTH: 50
<212> TYPE: DNA
<213> ORGANISM: artificial
<220> FEATURE:
<223> OTHER INFORMATION: probe sequence

<400> SEQUENCE: 9
aggtacattc atcctcacag attgcaaagg tgatttgggt ggggtttag                               50

<210> SEQ ID NO 10
<211> LENGTH: 50
<212> TYPE: DNA
<213> ORGANISM: Homo sapiens

<400> SEQUENCE: 10
ggtccccaaa gacgtcaatg cggccatcgc caccatcaag accaagcgca                              50

<210> SEQ ID NO 11
<211> LENGTH: 50
<212> TYPE: DNA
<213> ORGANISM: artificial
<220> FEATURE:
<223> OTHER INFORMATION: probe sequence

<400> SEQUENCE: 11
tcccaatggt gtagaccagt ggcgatggat ctaggagttt accaactgag                              50

<210> SEQ ID NO 12
<211> LENGTH: 50
<212> TYPE: DNA
<213> ORGANISM: artificial
<220> FEATURE:
<223> OTHER INFORMATION: probe sequence

<400> SEQUENCE: 12
tcccctgcca ccccccgggat ggctgcttcc aagttgtttg caattaaagg                             50

<210> SEQ ID NO 13
<211> LENGTH: 50
<212> TYPE: DNA
<213> ORGANISM: artificial
<220> FEATURE:
<223> OTHER INFORMATION: probe sequence

<400> SEQUENCE: 13
aggcaccttc agcgaggaca gcaaagggcg tctacagaga ccagccatat                              50

<210> SEQ ID NO 14
<211> LENGTH: 50
<212> TYPE: DNA
<213> ORGANISM: artificial
<220> FEATURE:

```
<223> OTHER INFORMATION: probe sequence

<400> SEQUENCE: 14
gctggtatat ccagtgcatt gttggcacca tgggaccaga aggtggtgac            50

<210> SEQ ID NO 15
<211> LENGTH: 50
<212> TYPE: DNA
<213> ORGANISM: artificial
<220> FEATURE:
<223> OTHER INFORMATION: probe sequence

<400> SEQUENCE: 15
agggtggctt gcagtccctg gcccttctgg tgggcatttg gtatgtcctt            50

<210> SEQ ID NO 16
<211> LENGTH: 50
<212> TYPE: DNA
<213> ORGANISM: artificial
<220> FEATURE:
<223> OTHER INFORMATION: probe sequence

<400> SEQUENCE: 16
cttcttgaac ctggtggccc ccgttggaac tatcagtggc gtctcccatg            50

<210> SEQ ID NO 17
<211> LENGTH: 13
<212> TYPE: PRT
<213> ORGANISM: artificial
<220> FEATURE:
<223> OTHER INFORMATION: peptide antigen
<220> FEATURE:
<221> NAME/KEY: MOD_RES
<222> LOCATION: (7)..(7)
<223> OTHER INFORMATION: PHOSPHORYLATION

<400> SEQUENCE: 17

Val Thr Thr Ala Leu Pro Ser Arg Gly Pro Ala Met Pro
1               5                   10
```

METHODS OF DETECTING PROGESTERONE RECEPTOR AND OF DETECTING AN EXPRESSION LEVEL

CONTINUING APPLICATION DATA

This application claims the benefit of U.S. Provisional Application Ser. No. 62/481,966, filed Apr. 5, 2017, and U.S. Provisional Application Ser. No. 62/500,694, filed May 3, 2017, each of which is incorporated by reference herein.

GOVERNMENT FUNDING

This invention was made with government support under CA159712 awarded by the National Institutes of Health. The government has certain rights in the invention.

SEQUENCE LISTING

This application contains a Sequence Listing electronically submitted to the United States Patent and Trademark Office via EFS-Web as an ASCII text file entitled "110-05710101_ST25.txt" having a size of 4 kilobytes and created on Apr. 3, 2018. Due to the electronic filing of the Sequence Listing, the electronically submitted Sequence Listing serves as both the paper copy required by 37 CFR § 1.8221(c) and the CRF required by § 1.821(e). The information contained in the Sequence Listing is incorporated by reference herein.

BACKGROUND

Estrogen and progesterone are potent breast mitogens. In addition to steroid hormones, multiple signaling pathways input to estrogen receptor (ER) and progesterone receptor (PR) actions via post-translational events. Protein kinases commonly activated in breast cancers phosphorylate steroid hormone receptors (SRs) and profoundly impact their activities.

Breast cancer is the most commonly diagnosed cancer in women (with at least 252,710 new cases estimated for 2017) and the second leading cause of cancer related death in women. Recent publications by The Cancer Genome Atlas (TCGA) Network and others have revealed fundamental molecular characteristics of breast cancer. Most notably, the four major breast cancer subtypes (luminal A, luminal B, human epidermal growth factor receptor 2 (HER2)-enriched, and basal-like) were identified and comprehensively analyzed revealing that breast cancers display a wide range of tumor heterogeneity caused by alterations in multiple factors, including somatically mutated driver genes (e.g. TP53, PIK3CA, AKT1, CBFB, GATA3, and MAP3K1, among others), gene amplifications (e.g., ERBB2), and hormonally regulated gene programs (driven primarily by estrogen, progesterone, and androgen steroids). Breast cancer subtypes can be further stratified. For example, recent TCGA analysis compared ductal and lobular histological subtypes, revealing new molecular factors strongly associated with lobular subtypes, including mutations that lead to activation of AKT and increased FOXA1 expression and activity (i.e. key inputs to amplified ER signaling). Despite these important findings, targeting the dominant molecular pathways has not been completely successful and many women experience tumor relapse after treatment with targeted therapies (i.e. ~40% of women receiving tamoxifen suffer relapse). Thus, a deeper mechanistic understanding of the complex molecular pathways that drive breast cancer progression and how they may emerge accompanied by more precise biomarkers is urgently needed to successfully impede tumor initiation, optimize and customize treatment strategies, as well as prevent disease progression while undergoing long-term (e.g., up to 10 years) endocrine therapy.

SUMMARY OF THE INVENTION

In some embodiments, this disclosure describes methods that can be used to determine if a patient is likely to respond to certain anti-cancer therapies and, in some embodiments, to certain anti-breast cancer therapies.

In one aspect, this disclosure describes a method that includes testing for the presence of a phosphorylated Ser294 (phospho-Ser294) progesterone receptor (PR) in a patient sample. In some embodiments, the method includes administering a therapeutically effective amount of a PR antagonist to the patient. In some embodiments, a therapeutically effective amount of a PR antagonist is administered to the patient only if phospho-Ser294 PR is detected.

In some embodiments, the patient can have been diagnosed with a breast cancer.

In some embodiments, the PR antagonist can block phosphorylation of Ser294 of the PR and/or may include at least one of onapristone, mifepristone, aglepristone, and WAY-348.

In some embodiments, testing for the presence of phospho-Ser294 PR can include bringing the patient sample into contact with an anti-phospho-Ser294 PR antibody and/or detecting the ability of a cell from the patient sample to form a secondary mammosphere.

In another aspect, this disclosure describes a method that includes: determining at least one expression sample level of at least one gene in a cell of a biological sample from a patient; and comparing the at least one expression sample level in a cell of the biological sample to at least one expression level of the at least one gene in a cell of a control sample. In some embodiments, the gene can include PGR, PAX2, AHR, AR, IRS-1, RUNX (also known as AML), and/or a RUNX-regulated gene, or any combination thereof.

In some embodiments, the method includes determining if the expression sample level of the at least one gene is decreased as compared to the control sample and/or determining if the expression sample level of the at least one gene is increased as compared to the control sample.

In some embodiments, the at least one gene includes a gene selected from the genes listed in Table 5B, Table 6B, Table 7B, Table 8B, Table 9B, or Table 10B and/or a gene selected from the genes listed in Table 4, Table 5A, Table 6A, Table 7A, Table 8A, Table 9A, or Table 10A.

In some embodiments, the patient can have been diagnosed with a breast cancer.

In some embodiments, the method includes administering a therapeutically effective amount of a PR antagonist to the patient. In some embodiments, the PR antagonist can block phosphorylation of Ser294 of the PR and/or may include at least one of onapristone, mifepristone, aglepristone, and WAY-348.

In a further aspect, this disclosure describes a method that includes: determining at least one expression sample level of at least one gene in a cell of a biological sample from a patient, and comparing the at least one expression sample level in a cell of the biological sample to at least one expression level of the at least one gene in a cell of a control sample. The at least one gene may be selected from the genes listed in Tables 4-10, or may include any combination of the genes listed in Tables 4-10.

In some embodiments, the method includes determining if the expression sample level of the at least one gene is decreased as compared to the control sample and/or determining if the expression sample level of the at least one gene is increased as compared to the control sample.

In some embodiments, the at least one gene includes a gene selected from the genes listed in Table 5B, Table 6B, Table 7B, Table 8B, Table 9B, or Table 10B and/or a gene selected from the genes listed in Table 4, Table 5A, Table 6A, Table 7A, Table 8A, Table 9A, or Table 10A.

In some embodiments, the patient can have been diagnosed with a breast cancer.

In some embodiments, the method includes administering a therapeutically effective amount of a PR antagonist to the patient. In some embodiments, the PR antagonist can block phosphorylation of Ser294 of the PR and/or may include at least one of onapristone, mifepristone, aglepristone, and WAY-348.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1(A-E) shows Total progesterone receptor (PR) and phospho-Ser294 PR immunohistochemistry (IHC) staining in cell lines, tissue sections, and in a breast cancer tissue microarray.

FIG. 2(A-D) shows PR Ser294 phosphorylation and total PR H-scores are not correlated and PR Ser294 phosphorylation H-scores were negatively associated with various tumor characteristics.

FIG. 3(A-F) shows proliferation and biomarker expression in breast tumor explants in response to estrogen (E2), progesterone (P4), or combined P4+U0126 treatment. FIG. 3C. Representative tumor explant IHC image after staining for total ER expression. FIG. 3D. Representative tumor explant IHC image after staining for total PR expression. FIG. 3E. Representative tumor explant IHC image after staining for pSer-294 PR expression. FIG. 3F. Representative tumor explant IHC image after staining for phospho-ERK1/2 expression.

FIG. 4(A-B) shows select PR antiprogestins, mifepristone and aglepristone, induce PR Ser294 phosphorylation, but onapristone does not.

FIG. 5(A-D) shows gene expression analysis in T47D cells treated with various ligand combinations demonstrate unique promoter selection.

FIG. 6(A-B) shows the phospho-Ser294 PR gene set is upregulated in infiltrating lobular carcinoma (ILC) breast tumors.

FIG. 7(A-F) shows RUNX2 may facilitate SUMO-deficient PR target gene expression.

FIG. 8(A-G) shows mammosphere Formation in T47D cells stably expressing either empty vector or various forms of the B isoform of PR (PR-B, PR-B K388R, or PR-B S294A) made as described in Knutson et al. *Breast Cancer Res* 2012, 14:R95. Primary (FIG. 8A) and secondary (FIG. 8B) mammosphere in T47D cells over-expressing empty vector, PR-B, PR-B K388R, or PR-B S294A and plotted as a percentage of Mammosphere Forming Efficiency (MFE; see Methods). Cells were treated with vehicle (EtOH) or R5020 (10 nM). FIG. 8C. Images of primary mammospheres (vehicle) from FIG. 8A. Primary (FIG. 8D) and secondary (FIG. 8E) mammospheres in T47D cells treated with vehicle (H2O) or EGF (20 ng/ml). Mammospheres were allowed to grow for 14 days prior to counting. FIG. 8F. Primary mammospheres in T47D cells (PR-B or K388R) expressing shGFP or shRUNX2. FIG. 8G. Images of primary mammospheres from FIG. 8F. Data is represented as the average±SD of three readings. *p<0.05,  p<0.01, * p<0.001 compared to empty vector control (vehicle).

FIG. 9(B-C) Model depicting PR action in normal breast (FIG. 9B) vs. during neoplastic luminal tumor progression (FIG. 9C). Phosphorylation of PR Ser294 and p-PR target gene expression (HER2, RUNX2, AR, AHR, PAX2) in the cancer stem cell (CSC) or neighboring tumor cell compartments may occur during early luminal tumor progression of ER+/PR+(luminal A type) breast cancers that progress towards ER+/PR-low (and HER2+) (luminal B type) tumors that are CSC-rich and thus more likely to become endocrine resistant. Early addition of anti-progestins to anti-estrogen/ER based therapies may prevent or delay the onset of endocrine therapy resistant luminal breast cancer recurrence.

DETAILED DESCRIPTION OF ILLUSTRATIVE EMBODIMENTS

Figure 1A:
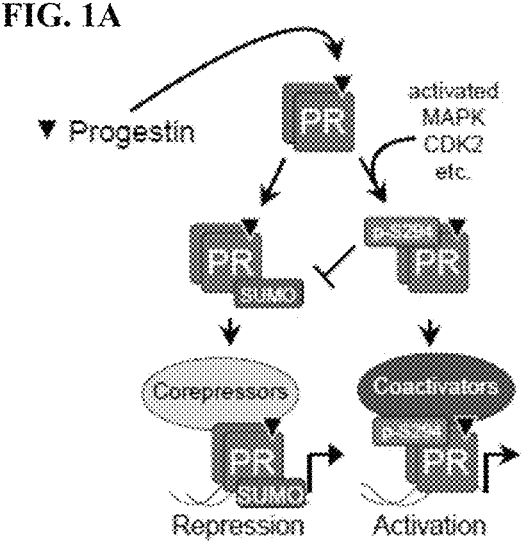
FIG. 1A. Cartoon depiction of PR ligand/kinase dependent Ser294 phosphorylation, which blocks Lys388 small ubiquitin-like modifier (SUMO)-ylation, and alters the recruitment of either co-activators or co-repressors resulting in promoter selective transcription.

This disclosure describes methods that, in some embodiments, can be used to determine if a patient is likely to respond to certain anti-cancer therapies and, in some embodiments, to certain anti-breast cancer therapies. In some embodiments, a method can include testing for the presence of a phosphorylated Ser294 (phospho-Ser294) progesterone receptor (PR). In some embodiments, a method can include determining the expression level of a gene in a patient sample and comparing it to a control sample.

As further described in an exemplary embodiment in Example 1, a subset of breast cancer patients that have tumors that express relatively low levels of PR and/or are clinically classified as PR-negative unexpectedly exhibit the presence of phosphorylated-PRs. As described in Example 1, in some tumors, phosphorylated-PRs may enable breast cancer progression. Thus, testing for the presence of phosphorylated PRs or for a change in the activity of a gene modulated by phosphorylated PRs allows for the identification of candidates for anti-progestin therapy and blockage of breast cancer progression. Anti-progestin therapy can include, for example, onapristone or similar anti-progestin or other agents that block PR phosphorylation.

In one aspect, this disclosure describes a method that includes testing for the presence of a phospho-Ser294 progesterone receptor (PR) in a patient sample. The PR can include both PR isoforms, PR-A and PR-B, derived from the PgR gene, and PR-A and/or PR-B can be phosphorylated at Ser294. Moreover, phosphorylation at Ser294 of PR-A, PR-B, or both can be involved in breast cancer stem cell expansion. In some embodiments, testing for the presence of phospho-Ser294 PR includes detecting phospho-Ser294 PR in the patient sample. In some embodiments, the method further includes administering a therapeutically effective amount of a PR antagonist to the patient.

A patient sample may be taken from any tissue or bodily fluid. The patient sample may include or may be derived from: blood; a tissue sample or biopsy; and/or cells isolated from the patient. In some embodiments the patient sample may preferable include breast tissue and/or a tumor biopsy. In some embodiments, a method described herein may include obtaining a patient sample from a patient.

In some embodiments, a therapeutically effective amount of a PR antagonist is administered only if phospho-Ser294 PR is detected. In some embodiments, if phospho-Ser294 PR is present, phospho-Ser294 PR will be detected. In some embodiments, phospho-Ser294 PR will be detected in a patient sample if phospho-Ser294 PR is increased compared to a control sample by at least 0.1%, at least 0.5%, at least 1%, at least 3%, at least 5%, at least 7%, at least 10%, at least 15%, at least 20%, at least 30%, at least 40%, at least 50%, at least 60%, at least 70%, at least 80%, or at least 90%. In some embodiments, phospho-Ser294 PR will be detected in a patient sample if phospho-Ser294 PR is increased compared to a control sample by up to 0.5%, up to 1%, up to 3%, up to 5%, up to 7%, up to 10%, up to 15%, up to 20%, up to 30%, up to 40%, up to 50%, up to 60%, up to 70%, up to 80%, up to 90%, up to 95%, or up to 100%.

Testing for the presence of phospho-Ser294 can include any suitable method. In some embodiments, testing for the presence of phospho-Ser294 PR can include bringing a patient sample into contact with an anti-phospho-Ser294 PR antibody. In some embodiments, the anti-phospho-Ser294 PR antibody can be tagged. In some embodiments, the anti-phospho-Ser294 PR antibody can be detected using a secondary antibody. In some embodiments, the anti-phospho-Ser294 PR antibody can be a polyclonal antibody. In some embodiments, the anti-phospho-Ser294 PR antibody can be a monoclonal antibody. In some embodiments, the antibody can recognize a peptide sequence including: C-PMAPGR(pS)PLATTV-amide (SEQ ID NO:17), where pS is phospho-Serine.

Testing for the presence of phospho-Ser294 may include probing for the upregulation of one, two, three, four, five, six, or more of the genes identified in Table 4, Table 5A, Table 6A, Table 7A, Table 8A, Table 9A, and Table 10A. Testing for the presence of phospho-Ser294 may include probing for the downregulation of one, two, three, four, five, six, or more of the genes identified in Table 5B, Table 6B, Table 7B, Table 8B, Table 9B, and Table 10B. Such probing may be used to validate and/or verify an anti-PR-phospho-Ser294 antibody. Additionally or alternatively, upregulation or down regulation of one or more of these genes may be used to detect high phospho-Ser294 PR in a patient sample.

In some embodiments, testing for the presence of phospho-Ser294 PR in a patient sample can include testing a portion of the patient sample for presence of phospho-Ser294 PR. Testing a portion of the patient sample can include, for example, testing a cell from the patient sample, testing a cell lysate from the patient sample, and/or testing a section of a patient sample. In some embodiments, testing for the presence of phospho-Ser294 PR in a patient sample can include testing a sample derived from the patient sample for presence of phospho-Ser294 PR.

In some embodiments, wherein testing for the presence of phospho-Ser294 PR can include detecting the ability of a cell from the patient sample to form a secondary mammosphere.

As further described in Example 1, progestin treatment may block proliferation in some strongly ER+/PR+ breast cancers, while stimulating proliferation in others, implicating PR as a master regulator of cell fate of both normal mammary epithelial and cancer stem/progenitor cell populations. Example 1 further reveals a key role for phospho-Ser294 PR in this aspect of PR-driven cell biology. As further described in Example 1, a subset of breast cancer patients whose tumors are clinically classified as PR-negative may have cancers driven in part by modest levels of highly transcriptionally active PRs that go undetected by clinical standards. Alternatively, abundant phospho-PRs may reside in minority cancer cell populations or "PR+ islands" within largely PR-null tumors capable of early dissemination. Patients harboring such tumors are strong candidates for anti-progestin therapy, including onapristone or similar agents that block phospho-Ser294 PR phosphorylation.

Figure 4A:
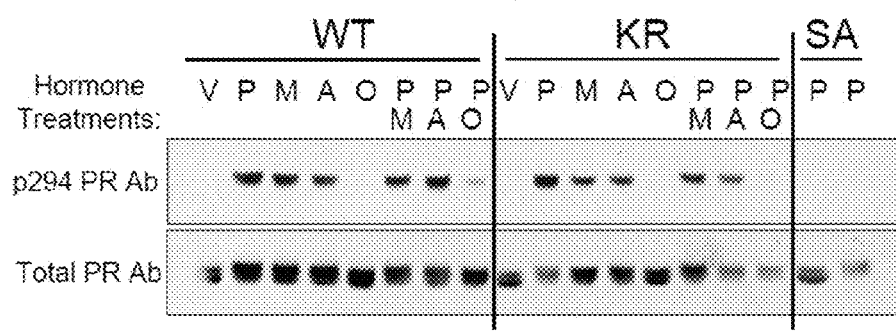
FIG. 4A. T47D cells expressing wild type (WT) PR or Ser294/SUMO-deficient PR (KR) were treated with vehicle (V), progesterone (P), mifepristone (M), aglepristone (A), onapristone (O), or a combination of progesterone and each antiprogestin. Cells were harvested for western blotting analysis. Both mifepristone and aglepristone induce PR Ser294 phosphorylation, whereas, onapristone does not. Co-treatment of progesterone and mifepristone or aglepristone also induced Ser294 phosphorylation, whereas, onapristone blocks Ser294 phosphorylation even in the presence of progesterone.
Figure 4B:
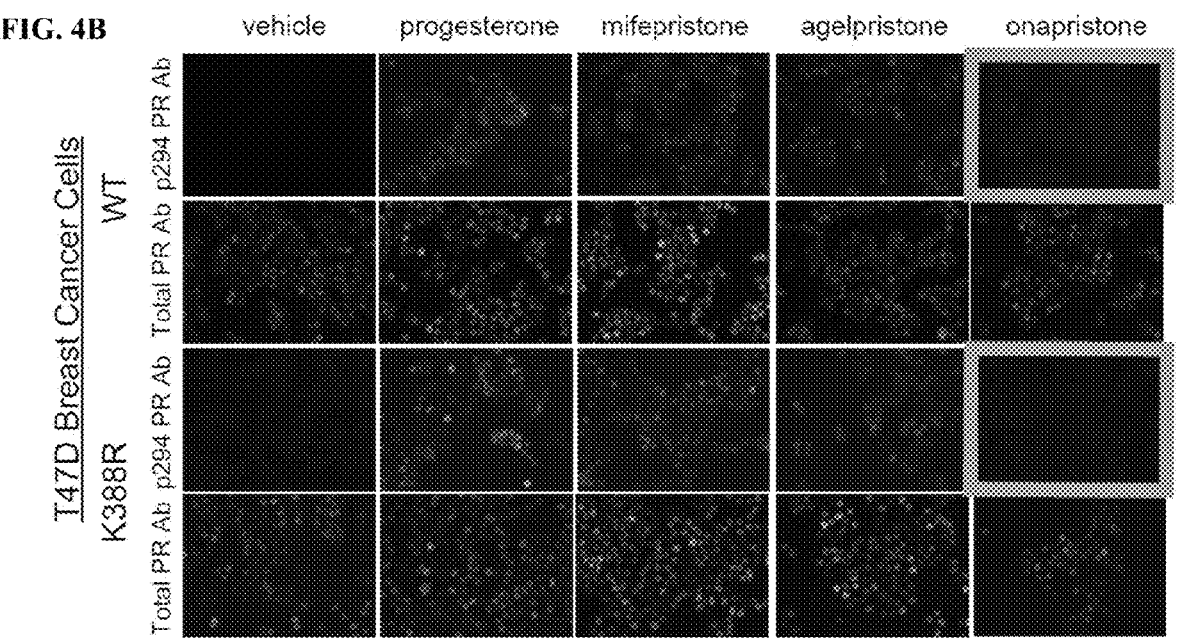
FIG. 4B. Similar to Western blotting analysis, T47D cells were treated as described above and analyzed for PR expression by immunofluorescence. Again, only onapristone effectively blocked PR Ser294 phosphorylation in both cells expressing WT or KR PR (highlighted with a green box).

As described in Example 1, commonly used PR ligands (agonists and antagonists alike) were found to induce PR Ser294 phosphorylation and phospho-PR target gene expression (FIGS. 4-5). Indeed, the partial agonist activity of antiprogestins appears to map to SUMO-deficient/phosphorylated receptors. Only onapristone was effective in blocking Ser294 phosphorylation and gene expression in cells expressing either wild type (WT) PR or SUMO-deficient (KR) PR (FIGS. 4-5). In contrast, in breast cancer cells expressing KR PR, mifepristone and aglepristone stimulated considerable Ser294 phosphorylation and gene regulation suggesting these antagonists may be less effective in cells that contain the highly transcriptionally active deSUMOylated PR.

In another aspect, this disclosure describes a method that includes determining at least one expression sample level of at least one gene in a cell of a biological sample from a patient; and comparing the at least one expression sample level in a cell of the biological sample to at least one expression level of the at least one gene in a cell of a control sample. In some embodiments, the method further includes administering a therapeutically effective amount of a PR antagonist to the patient. In some embodiments, a therapeutically effective amount of a PR antagonist may be administered depending on the results of the comparison. For example, a therapeutically effective amount of a PR antagonist may be administered only if the patient has a cancer and if it is determined that the cancer is likely to respond to therapeutic treatment with a PR antagonist.

Figure 11A:
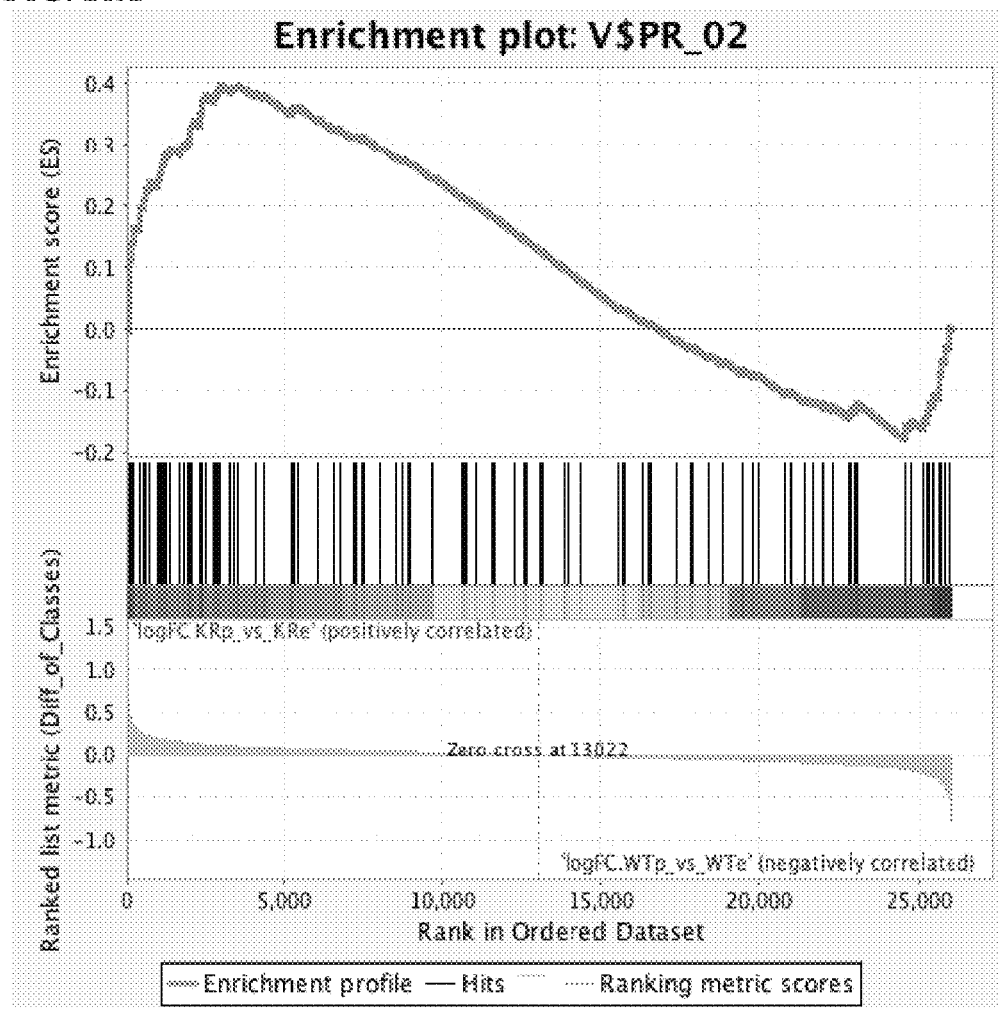
FIG. 11(A-F) shows gene set enrichment analysis (GSEA) in T47D breast cancer cells comparing KR+progestin vs. WT+progestin treatment groups. GSEA identified significantly regulated gene sets in the KR+progestin samples when compared to the WT+progestin samples. Five gene sets from the c3 MSigDB collection and one from the c6 collection are shown: genes containing PR DNA binding motifs (FIG. 11A), genes upregulated after ERBB2 overexpression in MCF-7 cells (FIG. 11B), genes containing androgen receptor DNA binding motifs (FIG. 11C), genes containing PAX family DNA binding motifs (FIG. 11D), genes containing AHR/ARNT DNA binding motifs (FIG. 11E), and genes containing AML1/RUNX binding motifs (FIG. 11F). These upregulated gene sets contain (respective) DNA binding motifs (above) near their transcriptional start sites, suggesting that these factors are important co-transcriptional regulators with PR in T47D cells expressing Ser294/SUMO-deficient PR (KR), compared to WT PR.
Figure 11B:
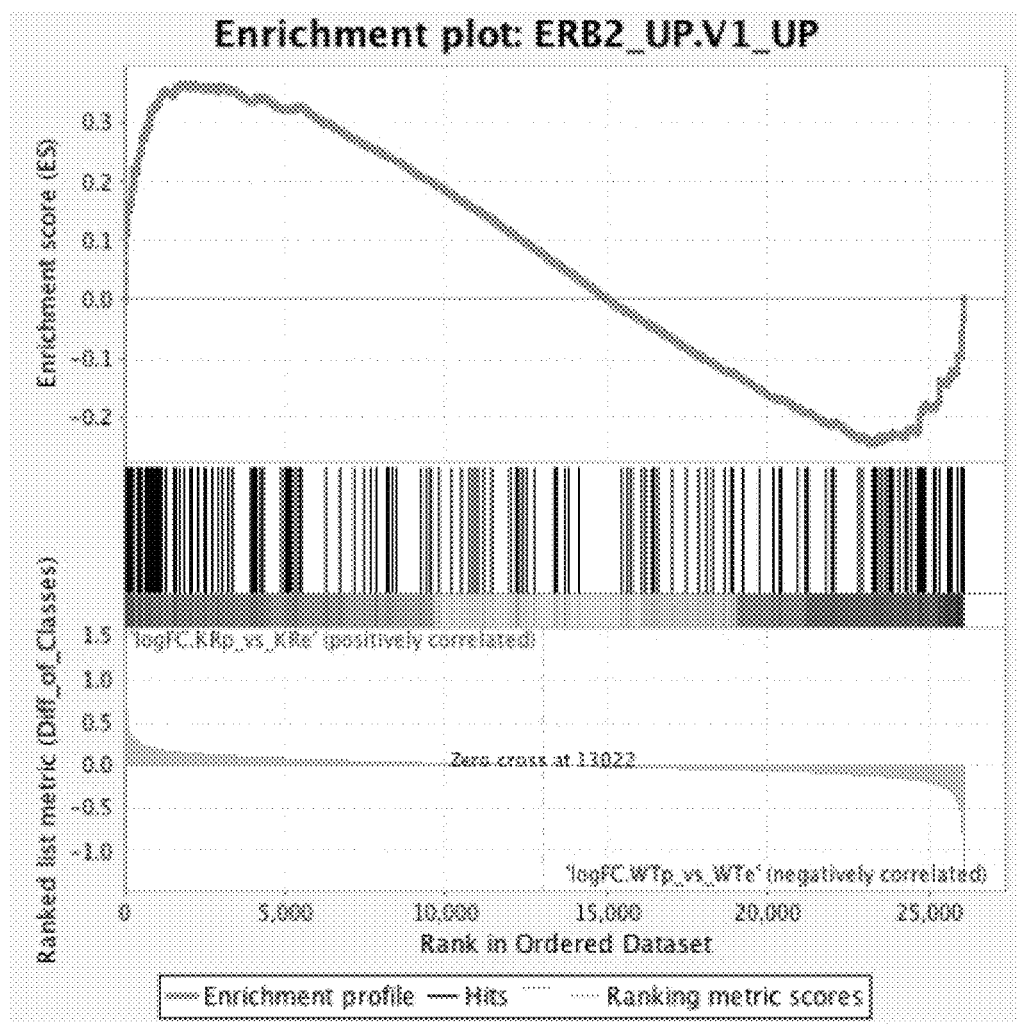
Figure 11C:
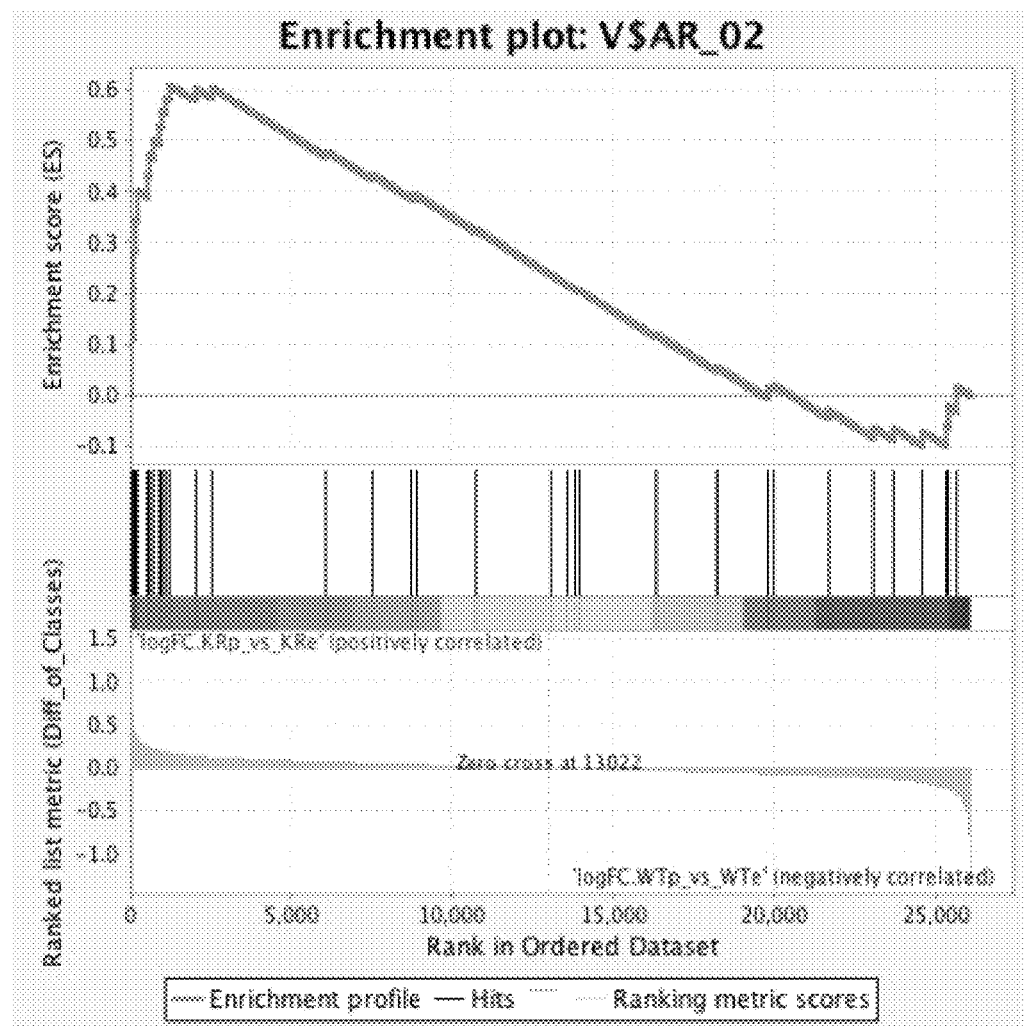
Figure 11D:
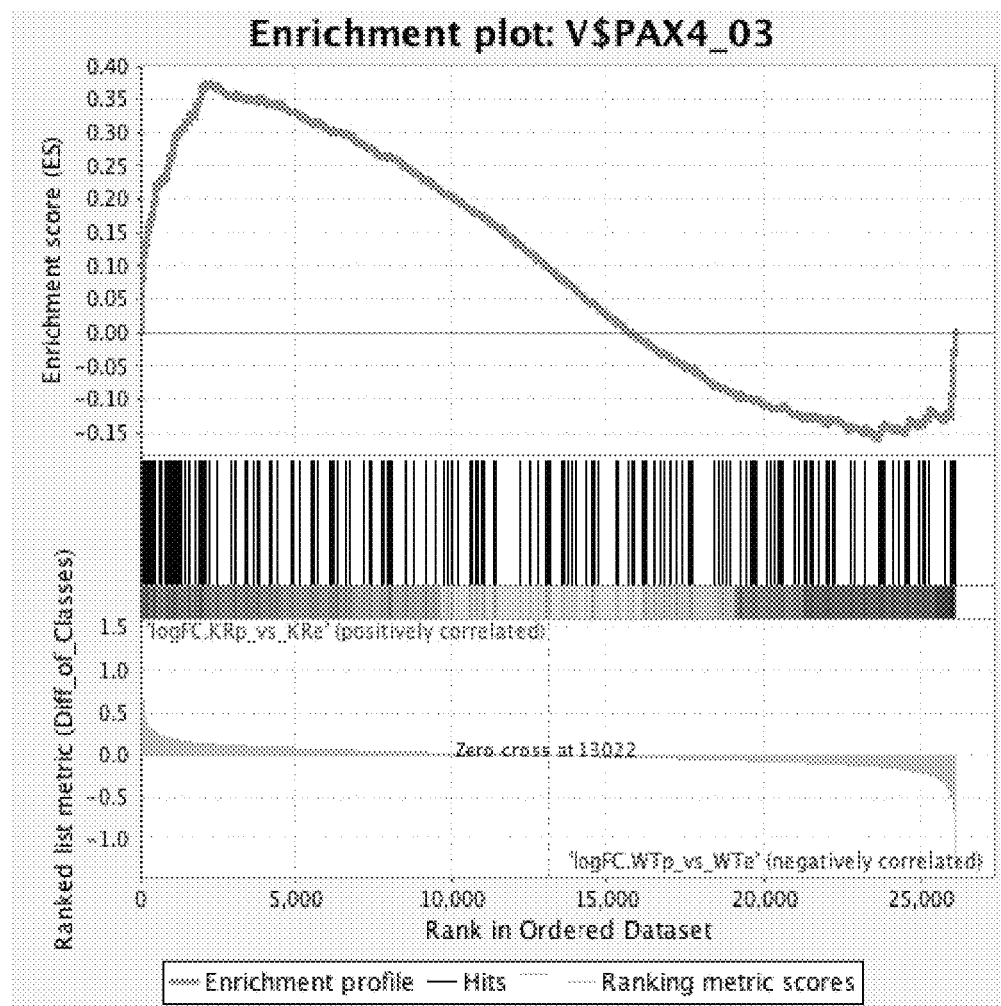
Figure 11E:
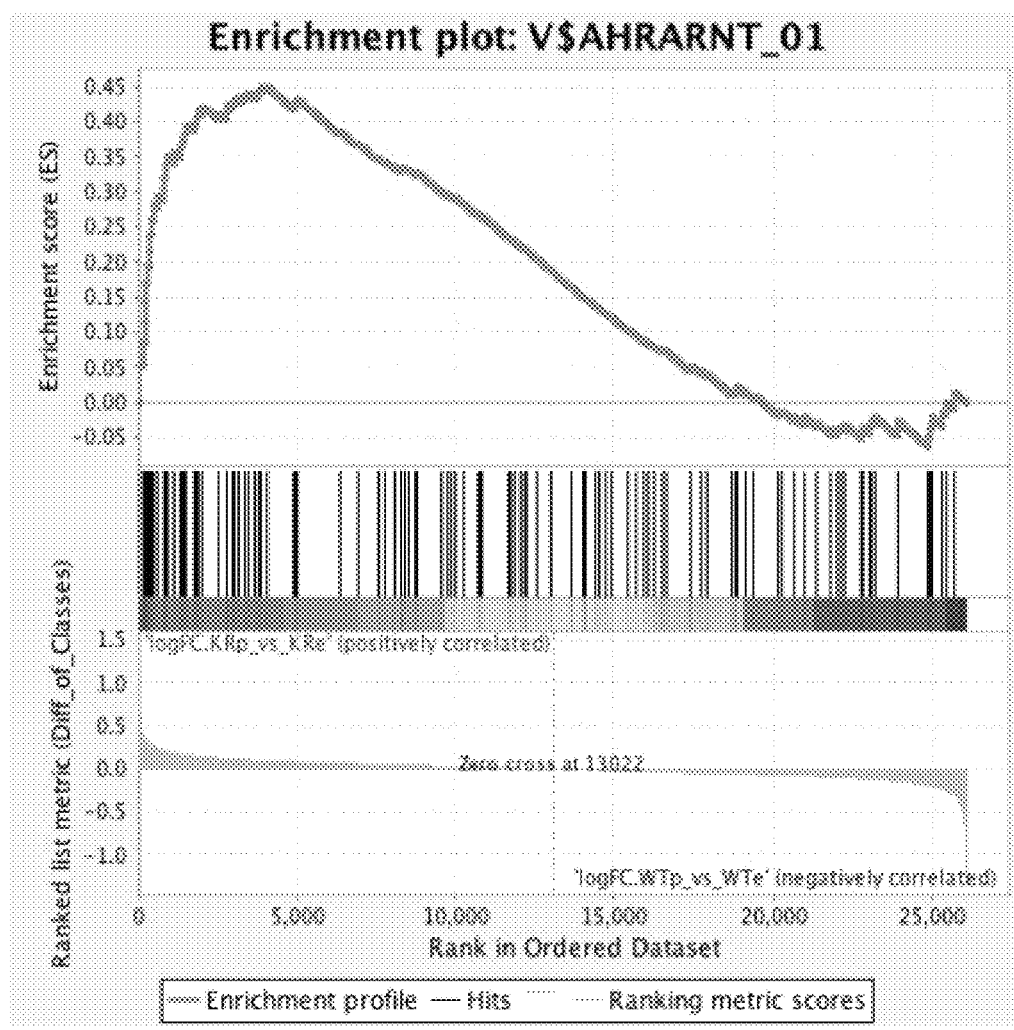
Figure 11F:
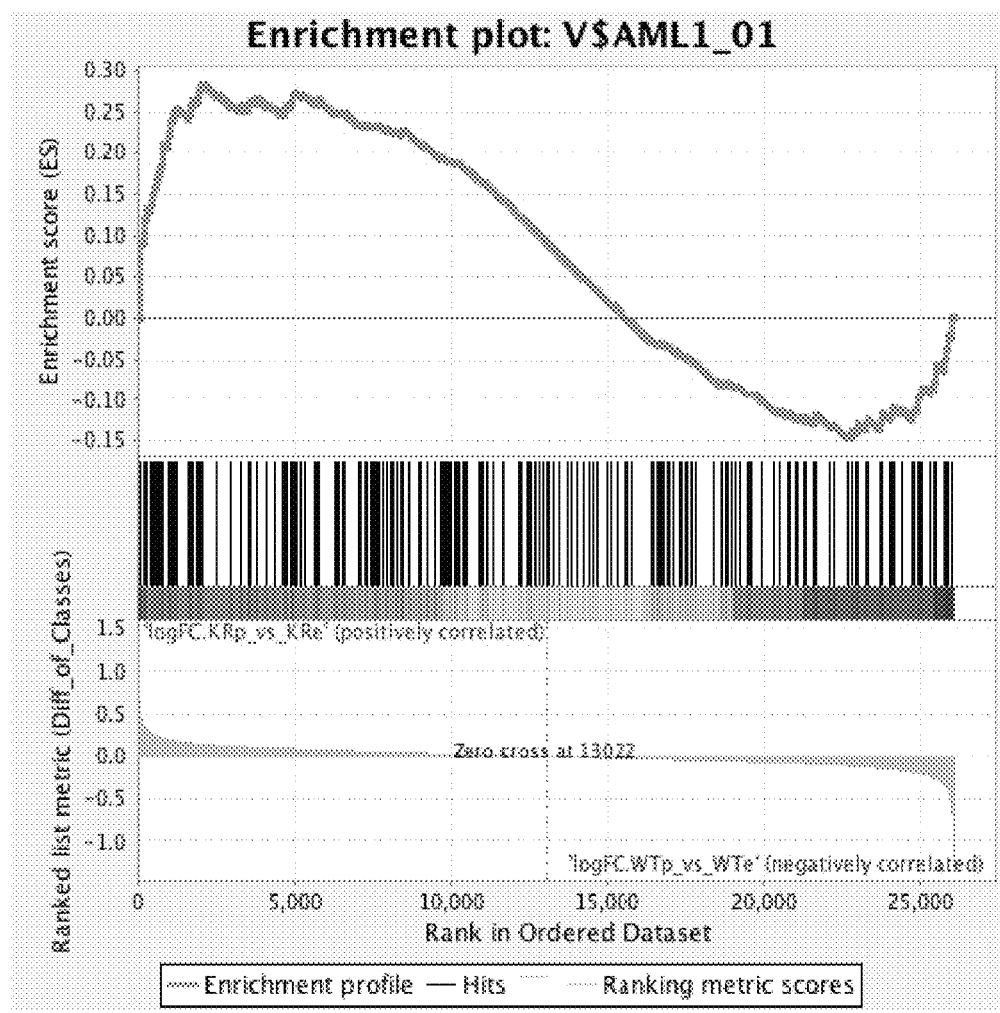

In some embodiments, the at least one gene can include the gene for progesterone receptor (PR) (PGR), PAX2, AHR, AR, IRS-1, RUNX (also known as AML), and/or a RUNX-regulated gene, or any combination thereof. In some embodiments, RUNX includes RUNX1, RUNX2, and/or RUNX3. In some embodiments, a RUNX-regulated gene includes SLC37A2. In some embodiments, a RUNX-regulated gene includes more than one gene targeted by RUNX. In some embodiments a RUNX-regulated gene includes at least one gene containing an AML1/RUNX binding motif (see, e.g., FIG. 11F).

In some embodiments, the at least one gene can include two genes, three genes, four genes, five genes, six genes, seven genes, eight genes, or more than eight genes.

For example, in some embodiments, the at least one gene can include PGR, PAX2, AHR, AR, IRS-1, and RUNX; in some embodiments, the at least one gene can include PGR, RUNX, and AHR; in some embodiments, the at least one gene can include PAX2 and AR; in some embodiments, the at least one gene can include IRS-1 and a RUNX-regulated gene. In some embodiments, a RUNX-regulated gene includes a gene listed in Table 9.

In some embodiments the at least one gene includes a gene identified in at least one of Tables 4-10. In some embodiments the at least one gene includes a combination of the genes listed in Tables 4-10.

In some embodiments, comparing the at least one expression sample level in a cell of the biological sample to at least one expression level of the at least one gene in a cell of a control sample can include comparing the expression sample level of at least one gene of Tables 5A, 6A, 7A, 8A, 9A, or 10A in a cell of the biological sample to the at least one expression level of the same gene or genes in a cell of a control sample. In some embodiments, the expression sample level may be increased compared to the expression level of the same gene or genes in a cell of a control sample. In some embodiments, a therapeutically effective amount of a PR antagonist may be administered only if the expression sample level of at least one gene of Tables 5A, 6A, 7A, 8A, 9A, or 10A in a cell of the biological sample is increased compared to the at least one expression level of the same gene or genes in a cell of a control sample.

In some embodiments, comparing the at least one expression sample level in a cell of the biological sample to at least one expression level of the at least one gene in a cell of a control sample can include comparing the expression sample level of at least one gene of Tables 5B, 6B, 7B, 8B, 9B, or 10B in a cell of the biological sample to the at least one expression level of the same gene or genes in a cell of a control sample. In some embodiments, the expression sample level may be decreased compared to the expression level of the same gene or genes in a cell of a control sample. In some embodiments, a therapeutically effective amount of a PR antagonist may be administered only if the expression sample level of at least one gene of Tables 5B, 6B, 7B, 8B, 9B, or 10B in a cell of the biological sample is decreased compared to the at least one expression level of the same gene or genes in a cell of a control sample.

In some embodiments, the method further includes obtaining the biological sample from the patient. The biological sample may be obtained by any suitable means including, for example, by biopsy. In some embodiments, the biological sample preferably includes a cancer cell. In some embodiments, the biological sample is preferably taken from tumor tissue.

In some embodiments, the patient can have been previously diagnosed with a cancer. In some embodiments, the cancer can include a breast cancer, an ovarian cancer, an endometrial cancer, a brain cancer, a lung cancer, a prostate cancer, an endometrial cancer, a meningioma or a uterine cancer.

In some embodiments, a control sample can include a sample from an individual other than the patient. In some embodiments, the control sample preferably includes normal tissue and/or non-cancerous tissue and/or tumor-free tissue. In some embodiments, a control sample can include a sample from an individual who has not been diagnosed with a cancer. In some embodiments, a control sample can include a sample from an individual who has not been diagnosed with the same cancer as the patient. In some embodiments, a control sample can include a sample from tissue of the same individual as the patient sample. In some embodiments, a control sample can include a cell from a biological sample from the patient who has been diagnosed with cancer wherein the biological sample does not contain a cancer cell. In some embodiments, a control sample can include normal-like tissue from the patient wherein the normal-like tissue was adjacent to tumor-containing tissue at the time of sampling.

In some embodiments, the patient is a mammal. In some embodiments, the patient is a human. In some embodiments, the patient is a cat.

In some embodiments, the method can further include determining if the expression sample level of at least one gene is decreased as compared to the control sample.

In some embodiments, the method can further include determining if the expression sample level of at least one gene is increased as compared to the control sample.

In some embodiments, if the expression sample level is increased or decreased as compared to the control sample, these changes may be used to determine whether the cancer will respond (e.g., experience cell death and/or decrease in size) to treatment with an anti-progestin (also referred to herein as a PR antagonist). For example, in some embodiments, if the expression sample level of RUNX and/or a RUNX-regulated gene is decreased as compared to the control sample, the cancer may respond to treatment with an anti-progestin. For example, in some embodiments, if the expression sample level of RUNX and/or a RUNX-regulated gene is decreased as compared to the control sample, the cancer may respond to treatment with an anti-progestin.

In some embodiments, the method can further include determining if a cancer is likely to respond to therapeutic treatment with a PR antagonist. For example, the method can include determining if the expression sample level of at least one gene is increased or decreased as compared to the control sample and using this information to determine if a cancer is likely to respond to therapeutic treatment with a PR antagonist. In some embodiments, for example, it may be determined that a cancer is likely to respond to therapeutic treatment with a PR antagonist only if the expression sample level of at least one gene of Tables 5A, 6A, 7A, 8A, 9A, or 10A in a cell of the biological sample is increased compared to the at least one expression level of the same gene or genes in a cell of a control sample. In some embodiments, for example, it may be determined that a cancer is likely to respond to therapeutic treatment with a PR antagonist only if the expression sample level of at least one gene of Tables 5B, 6B, 7B, 8B, 9B, or 10B in a cell of the biological sample is decreased compared to the at least one expression level of the same gene or genes in a cell of a control sample.

In some embodiments, the method can further include administering a therapeutically effective amount of a PR antagonist to the patient. In some embodiments, the method can further include administering at least one therapeutic agent in addition to a PR antagonist.

The PR antagonist can include any suitable PR antagonist. In some embodiments, the PR antagonist may block phosphorylation of Ser294 of a PR. In some embodiments, a PR antagonist can include onapristone, mifepristone, aglepristone, and/or WAY-348. In some embodiments, the method can also include administering at least one additional therapeutic agent.

As described in Example 1, RUNX2 is part of a phospho-PR-regulated pathway and is essential for mammosphere formation in PR-B+ cells (FIG. 8). For example, the data described in Example 1 suggest that cells growing in suspension no longer require exogenously added hormones but instead rely on growth factors to cue context-dependent (e.g., MAPK-dependent) phospho-PR actions, including gene expression of RUNX2. In addition, as with RUNX2 knock-down studies, secondary mammospheres failed to form in the presence of onapristone.

A "therapeutically effective" concentration or amount as used herein is an amount that provides some improvement or benefit to the subject. Desirable effects of treatment include preventing occurrence or recurrence of disease, alleviation of symptoms, diminishment of any direct or indirect pathological consequences of the disease, decreasing the rate of disease progression, amelioration or palliation of the disease state, and remission or improved prognosis. Likewise, the term "preventing," as used herein, is not intended as an absolute term. Instead, prevention refers to delay of onset, reduced frequency of symptoms, or reduced severity of symptoms associated with a disorder. Prevention therefore refers to a broad range of prophylactic measures that will be understood by those in the art. In some circumstances, the frequency and severity of symptoms is reduced to non-pathological levels. In some circumstances, the symptoms of an individual receiving the compositions of the invention are only 90%, 80%, 70%, 60%, 50%, 40%, 30%, 20%, 10%, 5%, or 1% as frequent or severe as symptoms experienced by an untreated individual with the disorder.

Therapeutically effective concentrations and amounts may be determined for each application herein empirically by testing the compounds in known in vitro and in vivo systems, such as those described herein, dosages for humans or other animals may then be extrapolated therefrom.

It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions and methods.

Toxicity and therapeutic efficacy of the compositions can be determined by standard pharmaceutical procedures in cell cultures or experimental animals, for example, for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compositions that exhibit high therapeutic indices can be preferred. The data obtained from cell culture assays and animal studies can be used in formulating a range of dosage for use in humans. The dosage of such compositions can preferably lie within a range of circulating concentrations that include the $ED_{50}$ with little or no toxicity. The dosage can vary within this range depending upon the dosage form employed and the route of administration utilized. The exact formulation, route of administration and dosage can be chosen by the individual physician in view of the patient's condition.

The present invention is illustrated by the following examples. It is to be understood that the particular examples,

EXAMPLES

Example 1

Example 1 shows post-translationally modified progesterone receptors direct ligand-specific expression of breast cancer stem cell-associated gene programs Methods Cell Culture and Reagents T47D human breast cancer cell lines engineered to stably express PR variants (null, WT, K388R, or S294A) were previously described (Knutson et al. *Breast Cancer Res* 2012, 14:R9). T47D cells were maintained in complete minimal essential medium (cMEM) supplemented with 5% fetal bovine serum (FBS), 1% non-essential amino acids (NEAA), 1% penicillin/streptomycin, 6 ng/ml insulin (Cell-Gro, Manassas, Va., USA, catalog #10-010-CV). T47D cells described above were engineered to also stably express RUNX2 shRNAs via the pLKO.1 knockdown expression vector system, which required 25 µg/ml puromycin for the vector. In various experiments, cells or explants were treated with E2, ICI 182 780, R5020, mifepristone, aglepristone, or onapristone (Arno Therapeutics, Inc., Flemington, N.J.).

Breast Tumor Explants

De-identified breast tumor samples were collected after surgery and immediately processed for tissue explant maintenance on sponges in cell culture medium, as previously described (Ravindranathan et al. *Nature Communications* 2013, 4:1923). Samples were derived from six patients pathologically diagnosed with invasive ductal carcinoma (IDC) and scored positive for ER (94-100%) and PR (1-100%), and negative for HER2 expression. Tissue explants were starved in media containing hormone-stripped FBS for 24 hours, and then treated for 48 hours with (1) vehicle, (2) 1 nM estradiol, (3) 10 nM estradiol, (4) 1 nM progesterone, (5) 10 nM progesterone prior to processing for quantitation of Ki-67 levels by IHC. Across treatment conditions, statistical significance was tested for using one-way analysis-of-variance (ANOVA) followed by pairwise testing of all treatment groups using the TukeyHSD post-test with R statistical software (R Core Team: R: A language and environment for statistical computing. *R Foundation for Statistical Computing*, Vienna, Austria 2015, [available on the world wide web at r-project.org/]). In additional experiments, six explants were similarly treated with estrogen or progesterone (2 hours) but in combination with 1 uM U0126 (to inhibit ERKs 1/2) and phospho-Ser294 PR levels were measured by IHC.

Immunohistochemistry, Immunofluorescence, and Immunoblotting

A custom phospho-specific antibody targeting PR Ser294 (clone 8508) was generated in rabbit against peptide sequence: C-PMAPGR(pS)PLATTV-amide (SEQ ID NO:17) (ThermoFisher Scientific, Waltham, Mass.). PR expression was measured by immunohistochemsitry methods: $1 \times 10^7$ Iscove's Modified Dulbecco's Medium (IMEM) starved T47D cell lines were treated, fixed in 10% neutral buffered formalin for 15 min, embedded in HistoGel (Richard-Allan Scientific, San Diego, Calif.), and embedded in paraffin blocks. Samples were sectioned, deparaffinized, microwaved for antigen retrieval in 10 mM sodium citrate, and stained according to the Vectastain Elite ABC peroxidase (catalog #PK-6101, Vector Labs, Burlingame, Calif.) and ImmPACT DAB kits (catalog #SK-4105, Vector Labs, Burlingame, Calif.). Slides were counterstained with hematoxylin before imaging.

Immunocytochemistry was performed on T47D cells expressing PR variants to measure total- and phospho-Ser294 PR levels. 500,000 cells were grown on coverslips in 6-well plates, starved in IMEM plus 5% charcoal stripped FBS, treated, and fixed with 4% paraformaldehyde for 20 min. The cells were permeabilized with 0.3% Triton-X100 before incubating with total-PR (clone Ab8, ThermoFisher Scientific, Waltham, Mass.) or custom phospho-Ser294-PR (clone 8508) antibodies. Cells were incubated with fluorescent secondary antibodies (Alexa Fluor 488) and DAPI mounting medium (Life Technologies, ThermoFisher Scientific, Waltham, Mass.) before visualizing on a Zeiss microscope with A4 and L5 filter cubes. Immunoblotting was performed as previously described (Daniel et al. *Mol Endocrinol* 2007, 21:2890-2906).

Tissue Microarray

A breast cancer tissue microarray (TMA) was generated by the University of Minnesota Histology and Immunohistochemistry Laboratory from 209 de-identified breast cancer samples. From this set, 151 tumor samples contained four different pathological regions that were independently included in the array: invasive, inflammatory, DCIS, and adjacent-normal-like (normal) tissue within tumor-containing tissue. Patient and tumor characteristics were extracted from pathological reports and used for analysis. Immunohistochemistry was performed on the TMA slides for total PR (antibody clone H190) or phospho-Ser294 PR (antibody clone 8508) expression levels (as described above). Stained slides were scanned using a Huron Technologies TISSUEscope LE by the University of Minnesota Imaging Facility and scored by pathologist (M.E.S.). The pathologist labeled each tissue spot according to staining percentage (percent of cells positive) and staining intensity (weak, moderate, strong). These two values were combined into a single histology score (H-score) that was used in subsequent analyses (Goulding et al. *Hum Pathol* 1995, 26:291-294; McCarty et al. *Arch Pathol Lab Med* 1985, 109:716-721). H-scores represent a combination of staining intensity and percent positive cells. H-scores range from 0-300, where the staining intensity score (negative (0), weak (1), moderate (2), or strong (3)) is multiplied by the percent positive cells. For example, an H-score of 20, could represent weak staining of 20% of the cells). For multiple regression analysis, H-scores were log 2 transformed and standardized prior to model fitting and feature selection. The linear model was fit using the glm function (family=gaussian) in the R statistical software.

Gene Expression Profiling

For genome-wide microarray expression analysis, T47D cells expressing pIRES-neo3 empty vector, WT PR, or K388R PR were serum starved in modified improved minimum essential media (IMEM) (Gibco, ThermoFisher Scientific, Waltham, Mass.) for one day before treatment. Eight groups were treated with vehicle control, progesterone ($10^{-8}$ M), mifepristone ($10^{-7}$ M), aglepristone ($10^{-7}$ M), onapristone ($10^{-7}$ M), or combined treatment of progesterone+mifepristone, progesterone+aglepristone, or progesterone+onapristone for six hours before RNA extraction using a RNeasy kit (QIAgen). DNase I treated (QIAgen) RNA samples from triplicate experiments were prepared for expression analysis using the Illumina HT-12v4 bead chip platform according to standard protocols. Raw data from agonist-treated cells (progesterone or R5020) collected from two identically performed independent experiments (from this study and a previous study: GSE34148 (Knutson et al. *Breast Cancer Res* 2012, 14:R95)) was combined, normalized, and batch-corrected to ensure that gene expression values were informative across samples from separate experiments. Data were analyzed within multiple common R (R Core Team: R: A language and environment for statistical computing. *R Foundation for Statistical Computing*, Vienna, Austria 2015, [available on the world wide web at r-project.org/]) and Bioconductor (Gentleman et al. *Genome Biol* 2004, 5:R80) packages. Raw intensities were log 2 transformed and quantile normalized using lumi (Du et al. *Bioinformatics* 2008, 24:1547-1548), batch corrected using sva (Leek et al.: sva: Surrogate Variable Analysis. R package version 3.18.0.), and multiple probes for a single gene were collapsed using genefilter (Gentleman et al.: genefilter: genefilter: methods for filtering genes from high-throughput experiments. R package version 1.52.1). Differentially expressed genes (pairwise comparisons between all eight groups) were analyzed in limma (Smyth: Limma: linear models for microarray data. In: *Bioinformatics and computational biology solutions using R and Bioconductor*. edn.: Springer; 2005: 397-420), where empirical Bayes was used to better estimate the variance of the genes. Biological comparisons (for example, R5020/vehicle) were presented as log 2 fold change including the Benjamini and Hochberg (BH) adjusted P value (Benjamini et al. *J Roy Stat Soc B Met* 1995, 57:289-300) to account for multiple hypothesis testing. Expression data is available in the GEO database, accession: GSE94363.

For reverse transcription quantitative polymerase chain reaction (RT-qPCR) assays, 5×105 cells/well were plated in six-well dishes, serum starved in modified IMEM for one day before treatment. RNA was extracted using TriPure reagent (Roche, Basel, Switzerland) and cDNA was created using the qScript cDNA SuperMix kit (Quanta Biosciences, Beverly, Mass.). Relative expression levels were determined by qPCR assays performed on a Roche Light-Cycler II using SYBR green master-mix (Roche, Basel, Switzerland). Target gene quantification levels were normalized to the expression of standard housekeeper genes: TBP, ACTB, 18S, and/or GAPDH.

Non-Negative Matrix Factorization and Hierarchical Clustering

Normalized gene expression data were filtered to isolate only high variance genes using the bioconductor package genefilter (Gentleman et al.: genefilter: genefilter: methods for filtering genes from high-throughput experiments. In., R package version 1.50.0 edn: R package version 1.50.0) using interquartile range cutoff value of 0.85. Non-negative matrix factorization (NMF) was performed within R using the NMF package version 0.20.5 (Gaujoux et al. *BMC bioinformatics* 2010, 11:367) where matrix factors were rank (2-10) and algorithm (brunet or snmf/r) optimized using the nmf function with parameters nrun=30 and seed=123456. Based on these results, the gene expression matrix was fully processed using the brunet algorithm, rank=5, nrun=150, seed=123456. Clustering and plots were performed in R (NMF package, a heat map function) using Euclidean distance and UPGMA (average) linkage.

T47D Signature Analysis within TCGA Samples

Gene expression data generated and published by the TCGA consortium (Cancer Genome Atlas Network: Comprehensive molecular portraits of human breast tumours. *Nature* 2012, 490:61-70) was downloaded from the TCGA data portal (available on the world wide web at tcga-data.nci.nih.gov/docs/publications/brca_2012/BRCA.exp.547.med.txt) and quantile normalized using the Bioconductor preprocessCore package (Bolstad: preprocessCore: A collection of pre-processing functions. In., R package version 1.30.0. edn: R package version 1.30.0). The downloaded data were provided as mean centered. Tumor sample metadata were downloaded from the TCGA publication including PAM50 molecular subtypes, ER, PR, and HER2 statuses. Tumors classified as Luminal A, Luminal B, or HER2-enriched and PR-negative (by IHC) were isolated from the dataset and further characterized. For each tumor, the mean expression value for the collection of genes within a gene set was plotted. From these values, the mean and 95% confidence interval was calculated and plotted. Gene sets were derived from experiments in T47D cells, for example: (1) genes upregulated by progestin in T47D cells expressing WT PR versus (2) genes upregulated by progestin in T47D cells expressing KR PR (Tables 2-3).

The ductal and lobular TCGA data was downloaded from the Sloan Kettering data freeze (freeze set 3/26/14) (available on the world wide web at cbio.mskcc.org/cancergenomics/tcga/brca_tcga) (Ciriello et al. *Cell* 2015, 163:506-519). The RNA-seq gene expression values (RSEM) were merged from 705 ductal and lobular samples. Downloaded values were provided as centered z-scores and were log 2 transformed across all genes before analysis. The mean expression values for genes within each gene set (PR or random) were plotted for each sample, according to their pathological characteristic (IDC, ILC, or mixed).

Gene Set Enrichment Analysis

Gene set enrichment analysis (GSEA) software (Subramanian et al. *Proc Natl Acad Sci USA* 2005, 102:15545-15550; Mootha et al. *Nat Genet* 2003, 34:267-273) was used to identify gene sets from the Molecular Signatures Database (MSigDB) collections 1-7 that were significantly regulated in cells stably expressing SUMO-deficient PR (K388R) compared to WT PR. The analysis compared two phenotype groups: KR+R502/KR−R5020 versus WT+R5020/WR−R5020. GSEA was executed using the default settings, except the permutation type was set to Gene_set with 1,000 permutations, and the metric for ranking genes was set to Diff_of_Classes because the dataset contained log-scale data.

Mammosphere Culture

Primary Mammospheres: Adherent cells were washed with PBS and dissociated enzymatically in 0.25% trypsin-EDTA (Invitrogen Corporation, Carlsbad, Calif.). Cells were sieved through a 40-μm sieve (BD FALCON, BD Biosciences, Bedford, Mass.) and analyzed microscopically for single-cellularity. Single cells were plated in ultra-low attachment plates (Corning, Inc., Corning, N.Y.) and cultured in a humid incubator. Cells were grown in a serum-free mammary epithelial basal medium (MEBM; Lonza Group, Basel, Switzerland) containing 1% B27 Supplement (Invitrogen Corporation, Carlsbad, Calif.), 1% penicillin-streptomycin (Invitrogen Corporation, Carlsbad, Calif.), 5 μg/ml insulin (Invitrogen Corporation, Carlsbad, Calif.), 20 ng/ml EGF (Sigma-Aldrich, St. Louis, Mo.), 1 ng/ml hydrocortisone (Sigma-Aldrich, St. Louis, Mo.), and 100 μM β-mercaptoethanol. Mammospheres were allowed to grow for approximately 14 days. Mammosphere Forming Efficiency (MFE) % was calculated by the number of mammospheres per well/number of cells seeded per well.

Secondary Mammospheres: Primary mammospheres were collected by centrifugation (5 min, 1000 rpm), and dissociated enzymatically in 0.25% typsin-EDTA. Cells were sieved through a 40-μm tip strainer (Bel-Art SP Scienceware, South Wayne, N.J.) and analyzed microscopically for single-cellularity. Single cells were plated in ultra-low attachment plates and cultured in a humid incubator. Cells were grown in conditioned media for approximately 14 days. The conditioned media consisted of a 1:1 mixture of mammosphere media (described above), and media from cultured parental cells. Mammosphere Forming Efficiency (MFE) % was calculated by the number of mammospheres per well/number of cells seeded per well.

Results

A Majority of Breast Tumors Contain Phospho-Ser294 PR

Figure 1B:
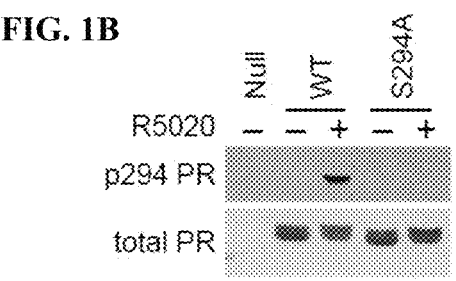
FIG. 1B PR Ser294 phosphorylation and total PR protein expression levels were measured in T47D breast cancer cell lines by western blotting, with and without progestin R5020 treatment.
Figure 1C:
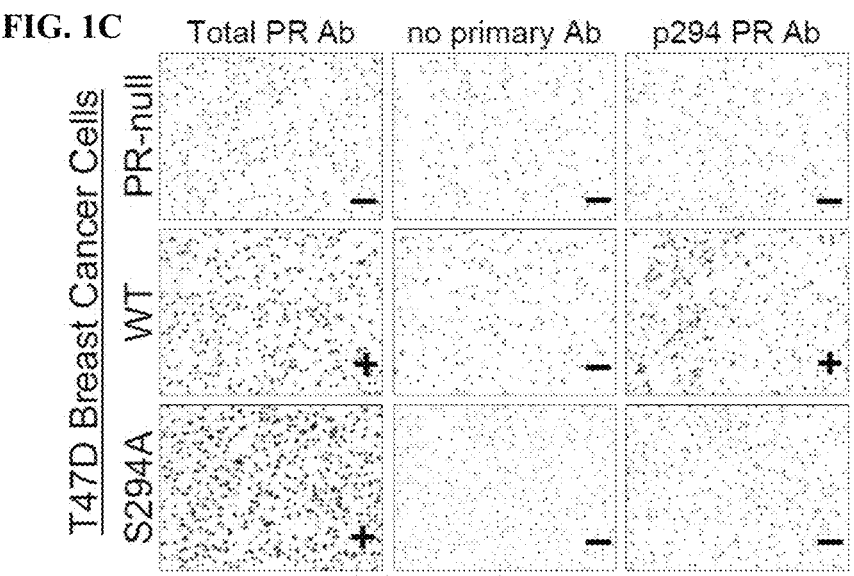
FIG. 1C. PR levels were also measured in T47D cells on cover slips using IHC methods.
Figure 1D:
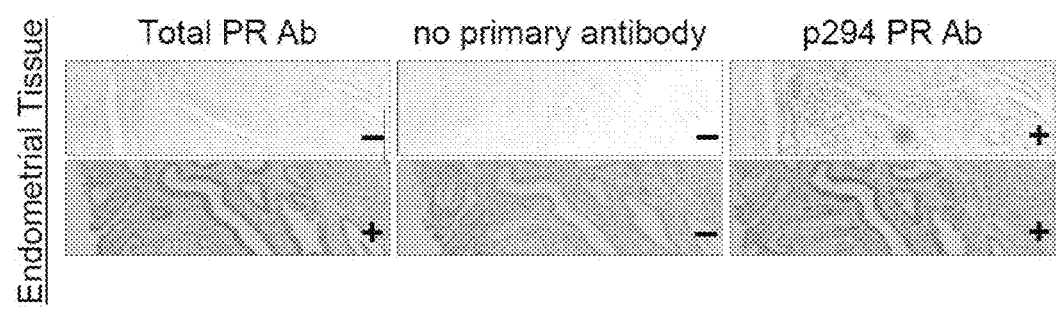
FIG. 1D. PR Ser294 and total PR protein levels were measured by IHC in a control tissue type (endometrial) to demonstrate effective PR Ser294 (and total PR) antibody specificity and sensitivity.
Figure 1E:
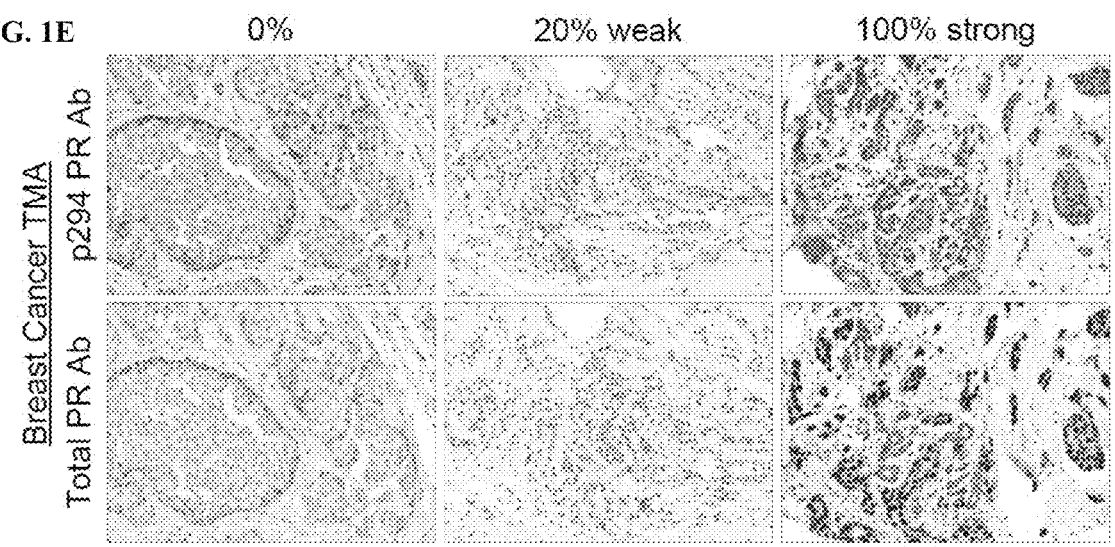
FIG. 1E. IHC in breast tumor sections (spots) of a tissue microarray. Six representative images demonstrate H-scoring classification: (column 1) 0% staining, (column 2) 20% positive cells, weak, (column 3) 100% positive cells, strong.

Functional roles for phosphorylation of PRs by mitogenic protein kinase pathways commonly elevated in breast cancers, including mitogen activated protein kinases (MAPKs), cyclin-dependent kinases (CDKs), and casein kinase 2 (CK2), have been demonstrated (Lange et al. *Proc Natl Acad Sci USA* 2000, 97:1032-1037; Shen et al. *Mol Cell Biol* 2001, 21:6122-6131; Pierson-Mullany et al. *Mol Cell Biol* 2004, 24:10542-10557; Hagan et al. *Nucleic Acids Res* 2013; Hagan et al. *Mol Cell Biol* 2011, 31:2439-2452; Daniel et al. *Proc Natl Acad Sci USA* 2009, 106:14287-14292). These events are predicted to enable gene promoter selection by uniquely modified PR species according to cell context (FIG. 1A). To demonstrate the prevalence of PR Ser294 phosphorylation in human luminal breast tumors in vivo, IHC staining of a tissue microarray (TMA) containing 209 patient breast tumors (split into 2,754 tissue spots) was completed for both total PR and phospho-Ser294 PR (Table 1). Note that phospho-Ser294 antibodies are unable to distinguish between PR isoforms. Thus, total and phospho-Ser294-specific PR antibodies were validated by performing Western blotting and IHC on PR-null and PR+T47D cells containing either WT PR-B or S294A mutant PR-B (FIG. 1B) and further optimized PR staining protocols for IHC using human PR+healthy uterine tissues (FIG. 1C). For the majority of tumor samples in the breast cancer TMA, four pathological regions of each tumor were identified by a clinical pathologist (designated as invasive, inflammatory, DCIS, or normal-like) and represented as separate tissue spots. Following staining with either total PR or phospho-Ser294 PR antibodies, a histological score (H-score) was calculated for each tissue spot based on the percent of positively stained cells and their staining intensity (strong, moderate or weak, FIG. 1D-E) (Goulding et al. *Hum Pathol* 1995, 26:291-294; McCarty et al. *Arch Pathol Lab Med* 1985, 109:716-721).

Figure 2A:
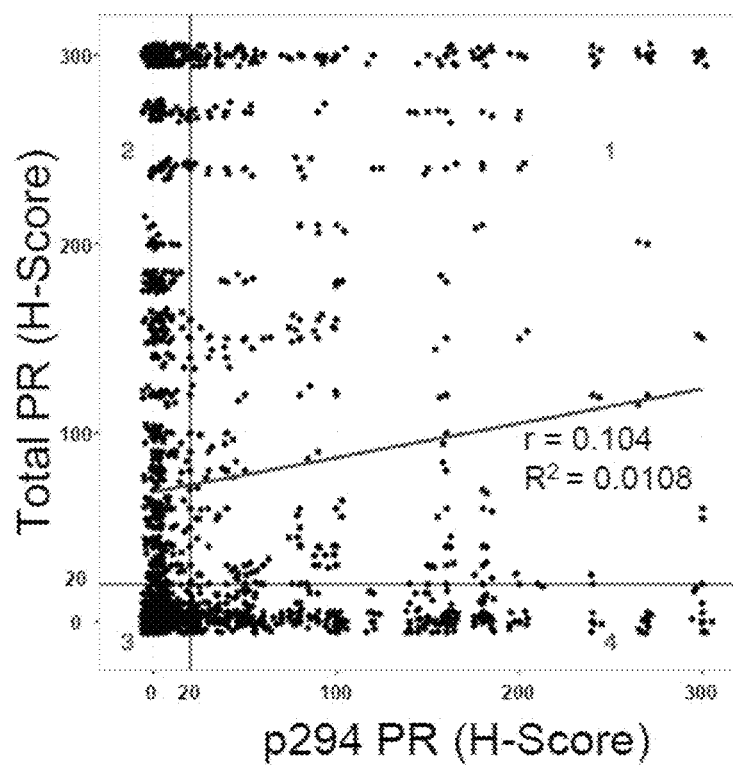
FIG. 2A. H-scores for total PR expression and phospho-Ser294 PR were compared among individual tumors spots from the TMA study. A Pearson correlation was calculated ($r=0.104$, $R^2=0.0108$). Tissue spots considered "positive" had an H-score of >20. Quadrants are labeled as further described herein.

As determined by a pathologist (see Methods), H-scores ranged from the minimum to maximum (0-300) and samples with H-scores>=20 were classified as positive. Overall, ~70% of tumors in this representative luminal tumor TMA stained positive for total PR. Of these PR+ samples, 54% were also positive for phospho-Ser294 PR expression. The percentage of tumors completely negative (H-score=0) for total PR staining was 15% and for phospho-Ser294 PR staining was 8%. Notably, total PR expression was not substantially correlated with the presence of Ser294 phosphorylated PR (r=0.104) in individual tumor spots, with some tumors having completely opposite total and phospho-Ser294 PR H-scores (FIG. 2A). Thus, these results reveal that phospho-Ser294 PRs can be readily detected in a significant subset of individual tumors that appear to express relatively low levels of total PR (quadrant 4, 19%). Conversely, ~23% of tumors (quadrant 2) expressed high total PR and low phospho-Ser294 PR. Thirty-nine percent of tumors were negative for both total PR and phospho-Ser294 PR (quadrant 3) while 17% of tumors were positive for both total and Ser294-phosphorylated receptors (quadrant 1). Positive staining for phospho-Ser294 PR was greatest in tissue spots pathologically classified as "Normal" (54%; normal-like tissue within tumor-containing tissue), followed by "DCIS" (47%), "Inflammatory" (43%), and "Invasive" sections having the lowest H-score levels for expression of phospho-Ser294 PR (38%). Positive staining for total PR levels by tissue type were: Normal (72%), DCIS (55%), Inflammatory (53%), and Invasive (52%). These data indicate that total PR and phospho-Ser294 PR staining are not directly related in this TMA as measured using distinct antisera and that PR levels are diminished in tissues with invasive characteristics relative to normal tissues or regions of DCIS.

TABLE 1

Breast cancer tissue microarray patient characteristics. The number and percentage of patient breast tumors included in the TMA study, stratified by various common breast tumor features.

|  | Number (n = 209) | Percent |
|---|---|---|
| ER/PR Status |  |  |
| ER-positive | 163 | 78.0 |
| ER-negative | 40 | 19.1 |
| PR-positive | 120 | 57.4 |
| PR-negative | 83 | 39.7 |
| ER-positive and PR-positive | 117 | 56.0 |
| ER-positive and PR-negative | 46 | 22.0 |
| ER-negative and PR-negative | 37 | 17.7 |
| Unknown | 6 | 2.9 |
| HER2 Status |  |  |
| HER2-positive | 59 | 28.2 |
| HER2-negative | 140 | 67.0 |
| Intermediate | 1 | 0.5 |
| Unknown | 9 | 4.3 |
| Lymph Node Status |  |  |
| LN-positive | 75 | 35.9 |
| LN-negative | 111 | 53.1 |
| Unknown | 23 | 11.0 |
| Grade |  |  |
| 1 | 34 | 16.3 |
| 2 | 96 | 45.9 |
| 3 | 66 | 31.6 |
| Unknown | 13 | 6.2 |
| Tumor Type |  |  |
| Invasive Ductal Carcinoma | 168 | 80.4 |
| Invasive Lobular Carcinoma | 21 | 10.1 |
| DCIS | 2 | 1.0 |
| Other | 14 | 6.7 |
| Unknown | 4 | 1.9 |
| Tumor Volume |  |  |
| <10 cm$^3$ | 64 | 30.6 |
| >=10, <20 cm$^3$ | 48 | 23.0 |
| >20 cm$^3$ | 68 | 32.5 |
| Unknown | 29 | 13.9 |

Figure 2B:
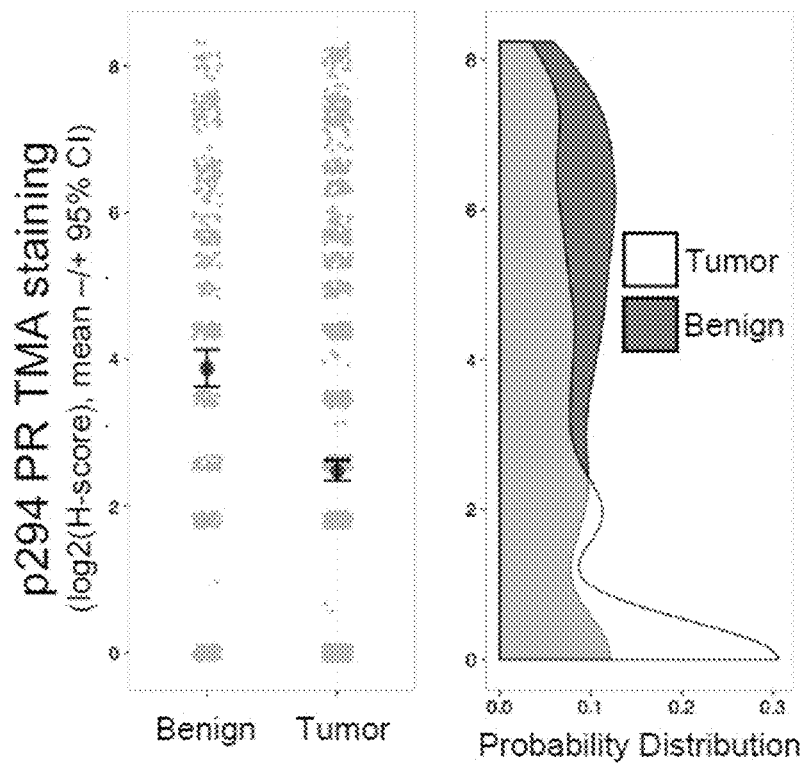
FIG. 2B. Left: Tissue microarray (TMA) spots were separated based on benign breast tissue (BBT) or tumor tissue (TT) pathological classification and PR Ser294 phosphorylation H-scores were plotted (grey dots) with mean values (black dots, −/+95% CI). Right: H-score densities reveal wide distributions for both groups, but H-scores among TT samples are skewed toward zero.
Figure 2C:
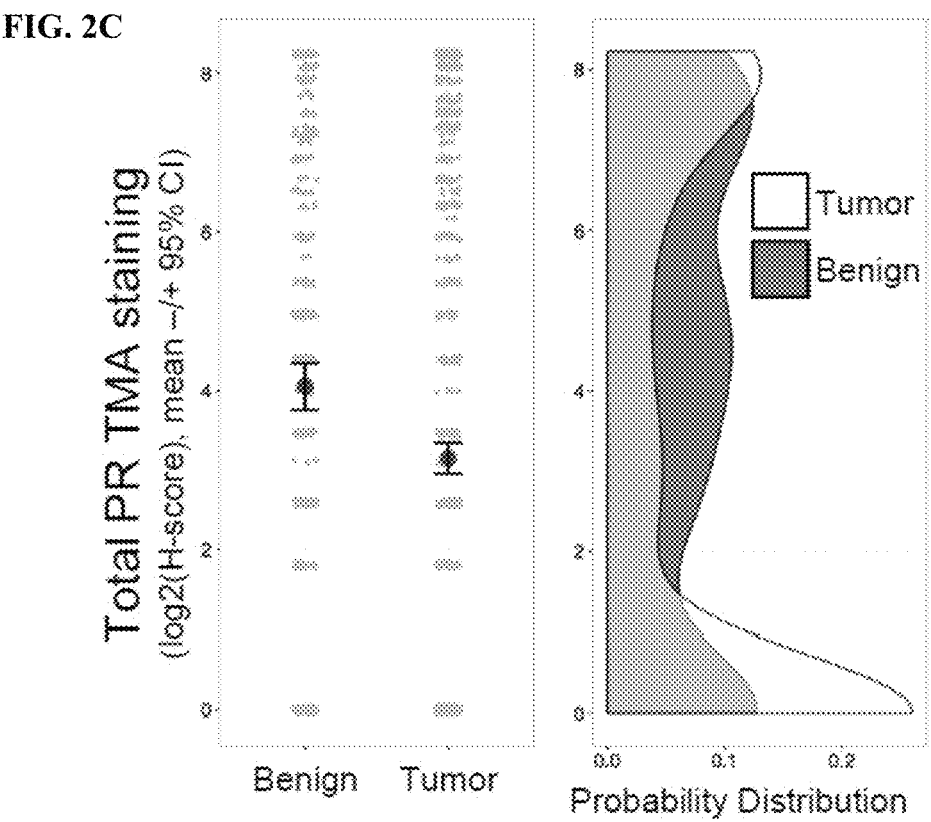
FIG. 2C. Left: Tissue microarray (TMA) spots and Right: H-score densities were prepared using the same analysis as FIG. 2B, except for total PR H-scores were used instead of PR Ser294 phosphorylation H-scores.
Figure 10:
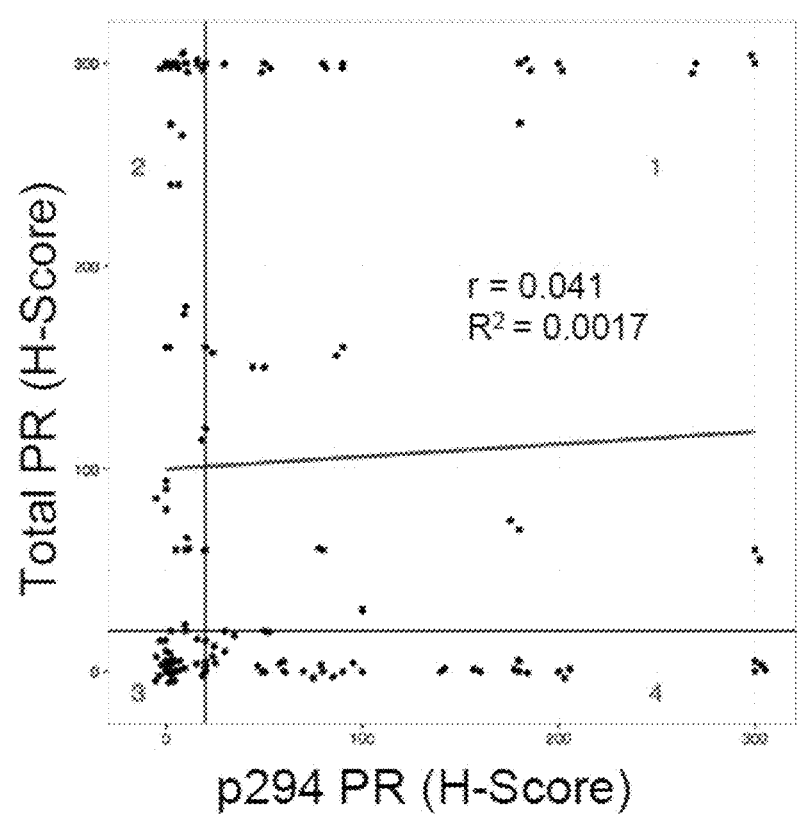
FIG. 10 shows PR Ser294 phosphorylation and total PR H-scores in only infiltrating lobular carcinoma (ILC) TMA tumor spots. H-scores for total PR expression and phospho-Ser294 PR were compared among individual tumors spots from the TMA study. A Pearson correlation was calculated (r=0.041, R2=0.0017). Tissue spots considered "positive" had an H-score of >20. Four quadrants were labeled as further discussed herein.

To test the hypothesis that lowered PR expression in tumors relative to benign breast tissue (BBT) is indicative of heightened (i.e. activated) PR transcriptional activity that occurs during the process of tumor progression, the levels of phospho-Ser294 PR or total PR expression between these two tissue classifications were compared. IHC scoring was completed by an independent breast cancer pathologist who also classified the tissue spot as BBT or tumor tissue (TT). H-scores among the BBT samples were significantly greater than the TT samples (Ser294: $P<2.2e-16$, Mann-Whitney test, FIG. 2B; total PR: $P<7.8e-06$, Mann-Whitney test, FIG. 2C). These data suggest that while both total and phospho-PR expression is varied within regions of established tumors, greater levels of both total and phospho-PR are typically found in epithelial layers displaying early lesions or normal-like pathology. Overall, the majority of tumors (TT) represented in this TMA contained less total PR/phospho-Ser294 PR relative to BBT. Interestingly, at least 7 tumors samples of infiltrating lobular carcinoma (ILC) were represented in the TMA as 173 spots. These tumors also expressed heterogeneous levels of total and phospho-Ser294 PRs. Phosphorylated PR levels were similar within each quadrant: 1-4 (29%, 20%, 21%, 27%) again bearing no direct relationship to total PR levels (FIG. 10).

Figure 2D:
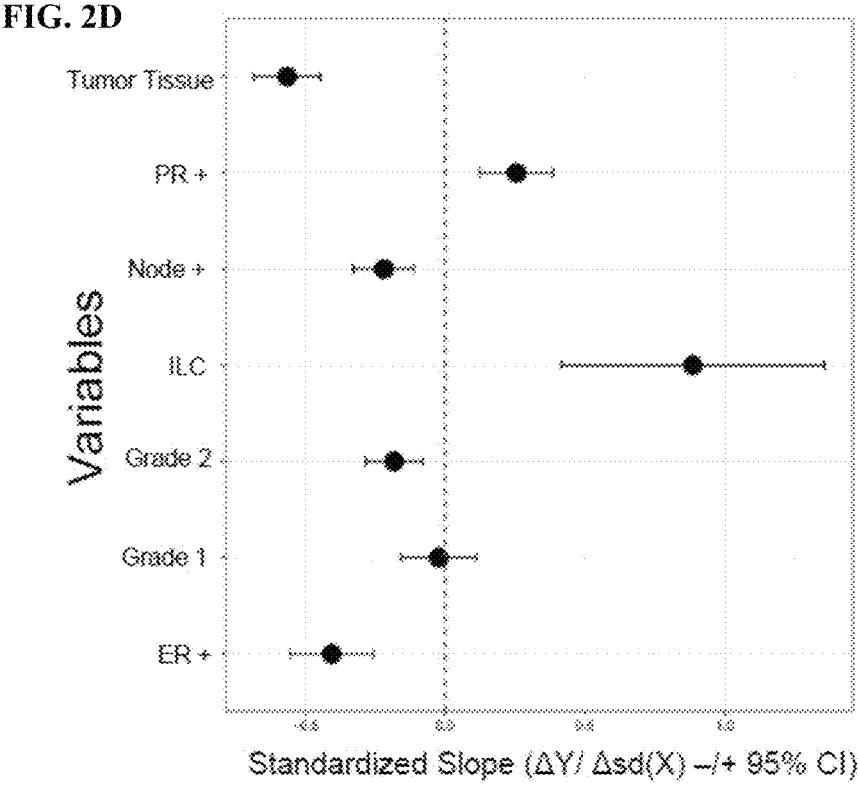
FIG. 2D. Using IHC staining scores and patient metadata from the breast cancer TMA study described herein, multiple regression was used to predict PR Ser294 H-scores from various factors. After backward elimination of non-significant variables, six variables remained significant, resulting in the following regression formula: $\text{H-Score}_{PR-Ser}294=0.40256-0.40579(\text{ER}_{Pos})+0.25459(\text{PR}_{Pos})-0.21988(\text{LN}_{Pos})+0.88609(\text{TumorType}_{ILC})-0.02332(\text{Grade}_1)-0.18223(\text{Grade}_2)-0.56517(\text{Tissue}_{Tumor})$. All variables were standardized prior to fitting the model and the coefficients are plotted with their respective 95% CI. Significant variables ($P<0.05$) have 95% confidence intervals (CIs) that do not overlap with the zero line.

Next, the relationship between PR Ser294 phosphorylation and the available patient tumor characteristics was probed (Table 1). Whether any of the tumor characteristics (independent variables) could predict PR Ser294 phosphorylation H-scores (dependent variable) using a multiple regression method was investigated. All independent variables were initially included in the model and non-significant variables were removed stepwise by backward elimination until a core set of significant variables remained. In this model, in addition to PR positivity (at clinical diagnosis) only infiltrating lobular carcinoma (ILC tumor type) was a significant indicator of PR Ser294 phosphorylation. Multiple factors were negative predictors of PR Ser294 phosphorylation: including tumor tissue pathology (vs. benign breast tissue), lymph node positivity (vs. node negativity), grade 3 status (vs. grade 2 or 1), and ER positive status (vs. negative status at clinical diagnosis) (FIG. 2D). These findings suggest that PR Ser294 phosphorylation is a relatively common but early event in breast cancer development. The presence of phospho-PR species may indicate that these early lesions contain sufficient levels of local progesterone and/or express activated MAPK or CDK signaling (i.e. downstream of growth factor receptors, for example) relative to tissues that are strongly PR+ but lack appreciable levels of phospho-Ser294 PR (i.e. expressing largely inactive/dephosphorylated and stable receptors) (Knutson et al. *Pharmacology & Therapeutics* 2014, 142:114-125; Daniel et al. *Mol Endocrinol.* 2007, 21:2890-2906).

Progesterone Treatment of Breast Tumor Explants Cultured Ex Vivo Drives Proliferation and Induces PR Ser294 Phosphorylation Because PR expression is primarily estrogen-induced in a majority of PR+ tissues and cancer models, isolating the unique contributions of progesterone/PR in breast cancer biology can be difficult to study in breast cancer models without the confounding (i.e. proliferative) effects of estrogen/ER. Therefore, the proliferative response to progesterone treatment in ex vivo 3D cultures of human breast tumor tissue (i.e. tumor explants) was tested. Fresh tumor fragments from ER+/PR+ tumors were dissected into 1 mm$^3$ sections and maintained on gelatin sponges submerged in cell culture medium as previously described (Ravindranathan et al. *Nature Communications* 2013, 4:1923; Dean et al. *Cell Cycle* 2012, 11:2756-2761; Diep et al. *Mol Cancer Res* 2016, 14:141-162). Explants were treated with 1 nM or 10 nM estrogen or progesterone for 48 hours before tumor fragments were embedded in paraffin, sectioned, and analyzed by IHC for Ki-67 expression. ER+ tumor explants treated with progesterone (10 nM) but not estrogen (1 nM and 10 nM) had a significantly higher percentage of Ki67-positive cells (a marker of cell proliferation), compared to vehicle treatment (P=0.006, ANOVA with TukeyHSD post-test; n=6) (FIG. 3A), Thus, progesterone (P4) treatment alone significantly stimulates proliferation in ex vivo breast tumor tissue samples.

Figure 3A:
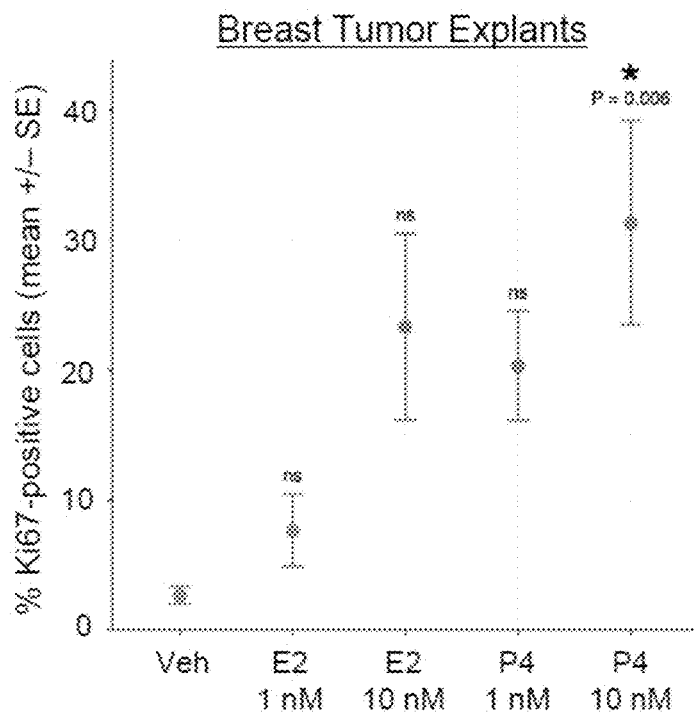
FIG. 3A. Post surgery, breast tumors were dissected and prepared for tissue explant experiments. Tumors were cut into small fragments and placed on sponges soaked in tissue culture medium. Sections were treated with vehicle (ethanol), E2 (1 or 10 nM) or P4 (1 or 10 nM) for 2.5 hours. Tissue sections were then fixed, embedded, and processed for Ki-67 IHC staining. The percent of Ki-67-positive cells were plotted (mean−/+SE). Comparing the groups via one-way analysis-of-variance (ANOVA), followed by Tukey HSD post-test, indicated that only the P4 (10 nM) treatment was significantly different from vehicle (P=0.0061, n=6 explants per treatment condition).
Figure 3B:
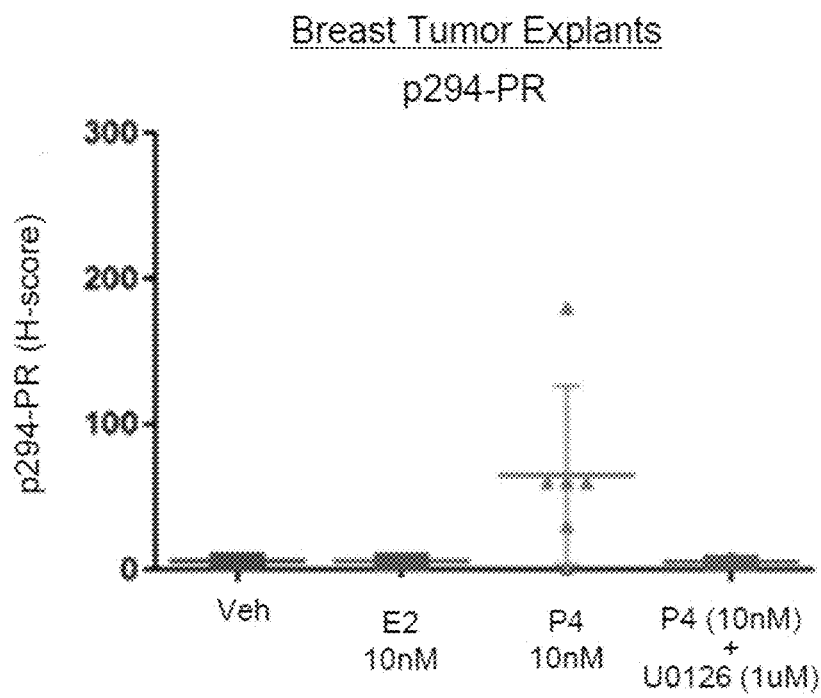
FIG. 3B. Breast tumor explants were treated with vehicle, estradiol (E2, 10 nM), progesterone (P4, 10 nM), or a combination of P4 and mitogen activated protein kinase (MAPK)-inhibitor U0126 (1 nM) for 2 hours. Explants were fixed, paraffin embedded, and stained for phospho-Ser294 PR expression and H-scores were plotted.

A proliferative and pro-survival role for MAPK-dependent phosphorylation of PR on Ser294 in breast cancer cells has been demonstrated (Knutson et al. *Breast Cancer Res* 2012, 14:R95). To assess whether PR Ser294 is a regulated phosphorylation site in human tumors ex vivo, the human tumor explant model was employed as above (FIG. 3A). ER+ luminal tumors were maintained as explants as above and instead treated with either vehicle or progesterone (10 nM) for 2 hours in the presence or absence of the MEK1/2 inhibitor U0126 (1 nM) prior to IHC staining using specific antibodies for total and phospho-Ser294 PR as well as ER-alpha and phospho-ERK1/2 (n=6; see Methods). As predicted, progesterone treatment induced robust PR Ser294 phosphorylation that was blocked by inclusion of the MEK inhibitor, U0126 (FIG. 3B). IHC staining demonstrated that all explants were ER+ and PR+(representative examples are shown; FIG. 3C-D). However, only progesterone treatment (P4) induced robust phosphorylation of PR Ser294 that was accompanied by activation of ERK1/2 (representative examples are shown; FIG. 3E-F). These data demonstrate that progesterone, at physiologic dose, is a potent mediator of breast tumor cell proliferation (independent of estrogen) in a model system that maintains breast tumor 3D structure, microenvironment, and epithelial cell polarity (known factors required for PR expression and paracrine actions (Graham et al. *Endocrinology* 2009, 150:3318-3326; Obr et al. *Mol Endocrinol* 2013, 27:1808-1824)) and indicate that PR-dependent transcriptional programs (i.e. that drive proliferation) including those enacted by MAPK-dependent phosphorylation of PR on Ser294 are likely to be activated in human breast cancers cultured ex-vivo.

Mifepristone and Aglepristone, but not Onapristone, Induce PR Ser294 Phosphorylation and Act as Partial Agonists PR antagonists have been examined for the treatment of PR-positive breast cancer with results comparable to tamoxifen (Jonat et al.: *Annals of Oncology* 2013, 24(10):2543-8; Robertson et al. *Eur J Cancer* 1999, 35:214-218). These agents have not been prioritized primarily because first-generation antiprogestins exhibited cross reactivity with glucocorticoid receptor (GR) and androgen receptor (AR) accompanied by intolerable toxicities in early trials. In addition, extensive luminal breast cancer heterogeneity may limit the ability to observe a subset of PR-driven breast cancers without patient selection. In this case, PR target gene expression may provide an accurate means of predicting which breast tumors are likely to be influenced by PR-driven biological pathways enacted by active phospho-Ser294 PRs. To probe changes in PR target gene expression in the presence or absence of commonly used PR ligands (R5020, RU486), including diverse antiprogestins (aglepristone, onapristone) currently in development for clinical use, the well characterized model system of T47D breast cancer cells, stably expressing either unmodified wild-type (WT) PR-B or a transcriptionally hyperactive form of deSUMOylated K388R PR-B (KR; this receptor faithfully mimics phosphorylated PR-B with regard to target gene selection) were used (Knutson et al. *Pharmacology & therapeutics* 2014, 142:114-125; Daniel et al. *Mol Endocrinol* 2007, 21:2890-2906). Whether the antiprogestins mifepristone (also called RU486), aglepristone, or onapristone alter PR Ser294 phosphorylation were tested in these T47D breast cancer models. Cells were treated for 1 hour with vehicle, progesterone, mifepristone, aglepristone, or onapristone and whole cell lysates were processed for Western blotting or immunofluorescence (IF) analysis (FIG. 4A, B). Progesterone treatment stimulated PR Ser294 phosphorylation in cells expressing either unmodified PR (WT) or SUMO-mutant (KR) PR. Similarly, in cells expressing either WT or activated KR PR, mifepristone and aglepristone stimulated robust PR Ser294 phosphorylation, whereas onapristone alone had no effect on PR Ser294 phosphorylation. Liganded PRs exhibited a slight gel mobility upshift (FIG. 4A) due to multiple phosphorylation events that occur within the PR N-terminus. Greater loss of total KR PR protein was also apparent in the presence of progesterone and selected antiprogestins relative to liganded WT PR, consistent with increased turnover of deSUMOylated active receptors relative to intact WT PRs. Notably, only onapristone blocked Ser294 phosphorylation in the presence of progesterone. These data show that PR Ser294 phosphorylation is stimulated by multiple ligands including common PR antagonists mifepristone and aglepristone. However, onapristone treatment does not permit Ser294 phosphorylation, even in the presence of progesterone, predicting that cells treated with this ligand will exhibit distinct gene expression profiles relative to other ligands (i.e. both agonists and antagonists) that stimulate PR Ser294 phosphorylation.

Figure 5A:
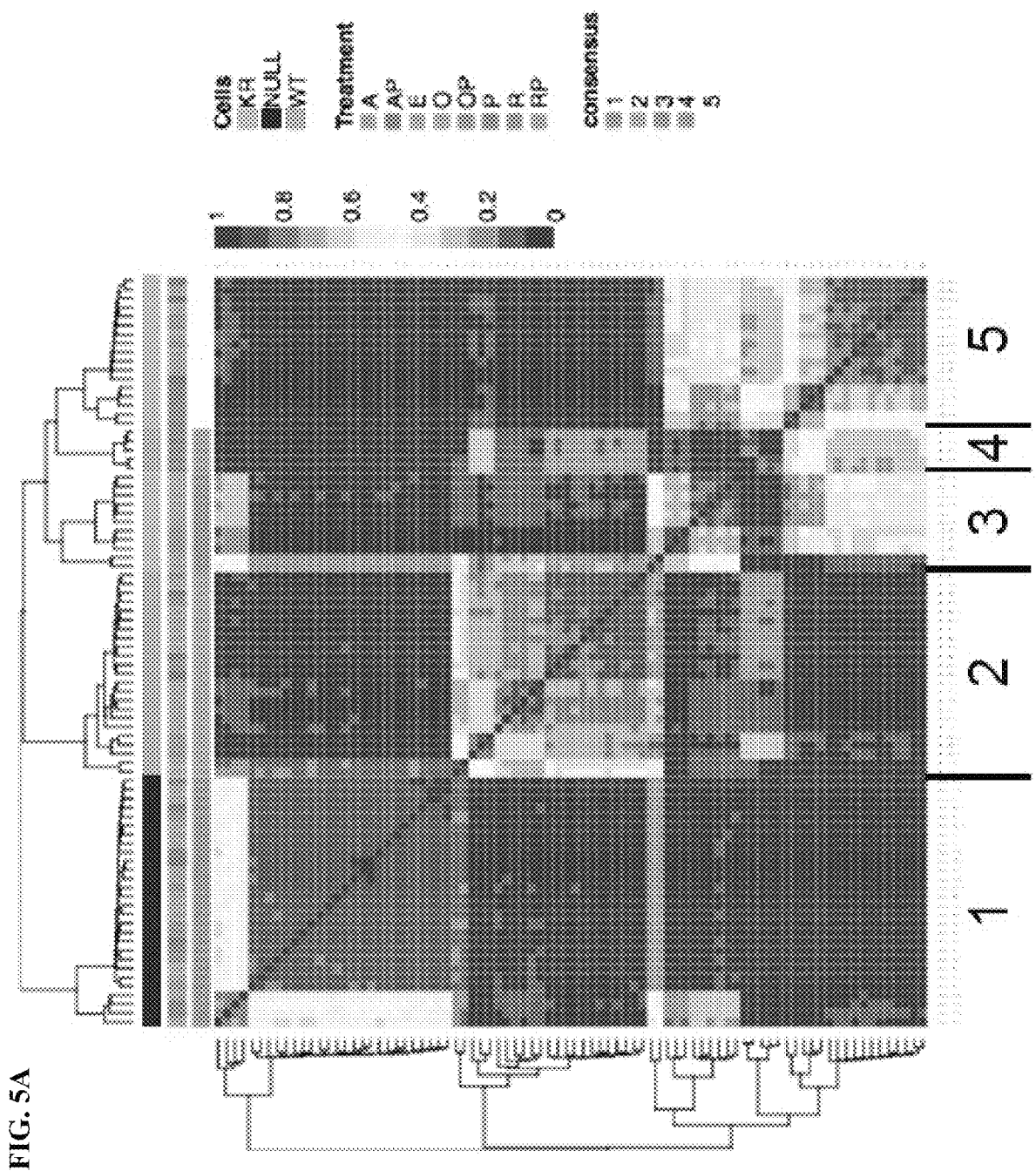
FIG. 5A. Gene expression arrays were used to measure global changes in gene expression levels in T47D cells treated with different PR ligands: vehicle, progestin (P), mifepristone (M), aglepristone (A), onapristone (O), P+M, P+A, or P+O. Genes under high variance across these samples were isolated and expression values were used for non-negative matrix factorization (NMF) clustering. Presented is the consensus matrix that indicates five major clusters are present in the samples.

PR ligand-mediated promoter selectivity remains understudied, especially in the context of antiprogestins and posttranslationally modified PR species. Breast tumors clearly express phosphorylated PR molecules (FIGS. 1E and 2A above) predicted to be deSUMOylated and transcriptionally hyperactive at a subset of SUMO-sensitive and phosphorylation-dependent gene promoters Knutson et al. *Breast Cancer Res* 2012, 14:R95. To further explore altered phospho-PR promoter selectivity (FIG. 1A), global gene expression analyses in T47D breast cancer cells expressing either WT or K388R PR-B receptors treated as above were conducted (FIG. 4A). PR-null cells or cells expressing unmodified WT or SUMO-deficient KR PR species were serum-starved (24 hours) prior to ligand treatment (6 hours). Cells were then treated with vehicle control (ethanol), progesterone (P), mifepristone (M), aglepristone (A), onapristone (O), or combined (progesterone agonist plus each antagonist) treatments of P+M, P+A, or P+O. Total RNA was collected and subjected to microarray gene expression analysis using the HT-12v4 beadchip platform (Illumina, San Diego, Calif.). The normalized gene expression dataset included 84 different samples under the above treatment conditions, necessitating identification of commonly regulated sample clusters (i.e. groups of similarly regulated samples) in an unbiased manner. First, genes were isolated under high variance and non-negative matrix factorization (NMF) analysis was performed (see Methods for details) (Lee et al. *Nature* 1999, 401:788-791; Gao et al. *Bioinformatics* 2005, 21:3970-3975; Kim et al. *Bioinformatics* 2007, 23:1495-1502; Brunet et al. *Proc Natl Acad Sci USA* 2004, 101:4164-4169.). The resulting consensus matrix indicated five uniquely regulated sample clusters within the gene expression dataset (FIG. 5A). Annotating the consensus matrix with cell line and treatment labels revealed five sample clusters: (1) PR-null cells (all treatments), (2) WT cells (all antiprogestin and vehicle treatments), (3) KR cells (onapristone and vehicle treatments), (4) WT cells (progestin treatments), and (5) KR cells (progestin, aglepristone, and mifepristone treatments) (FIG. 5A). These data clearly show that in cells expressing activated PR (i.e. KR or deSUMOylated PR), the antiprogestins mifepristone and aglepristone significantly regulated a similar gene expression program as progestin agonists (progesterone or R5020). Further, depending on the phosphorylation/SUMOylation status of PR, the receptor regulates completely different target genes when bound to different classes of antiprogestin (mifepristone/aglepristone vs. onapristone). The antiprogestins aglepristone and mifepristone substantially regulate multiple genes in cells expressing KR PR, but not WT PR, whereas in contrast, onapristone does not substantially regulate PR target genes in either cell line. These data suggest that the status of PR post-translational modifications can substantially impact PR target gene selectivity in a ligand-selective manner. Namely, deSUMOylated (KR) PRs recognize selected antagonists (mifepristone and aglepristone) as potent receptor agonists relative to onapristone.

Figure 5B:
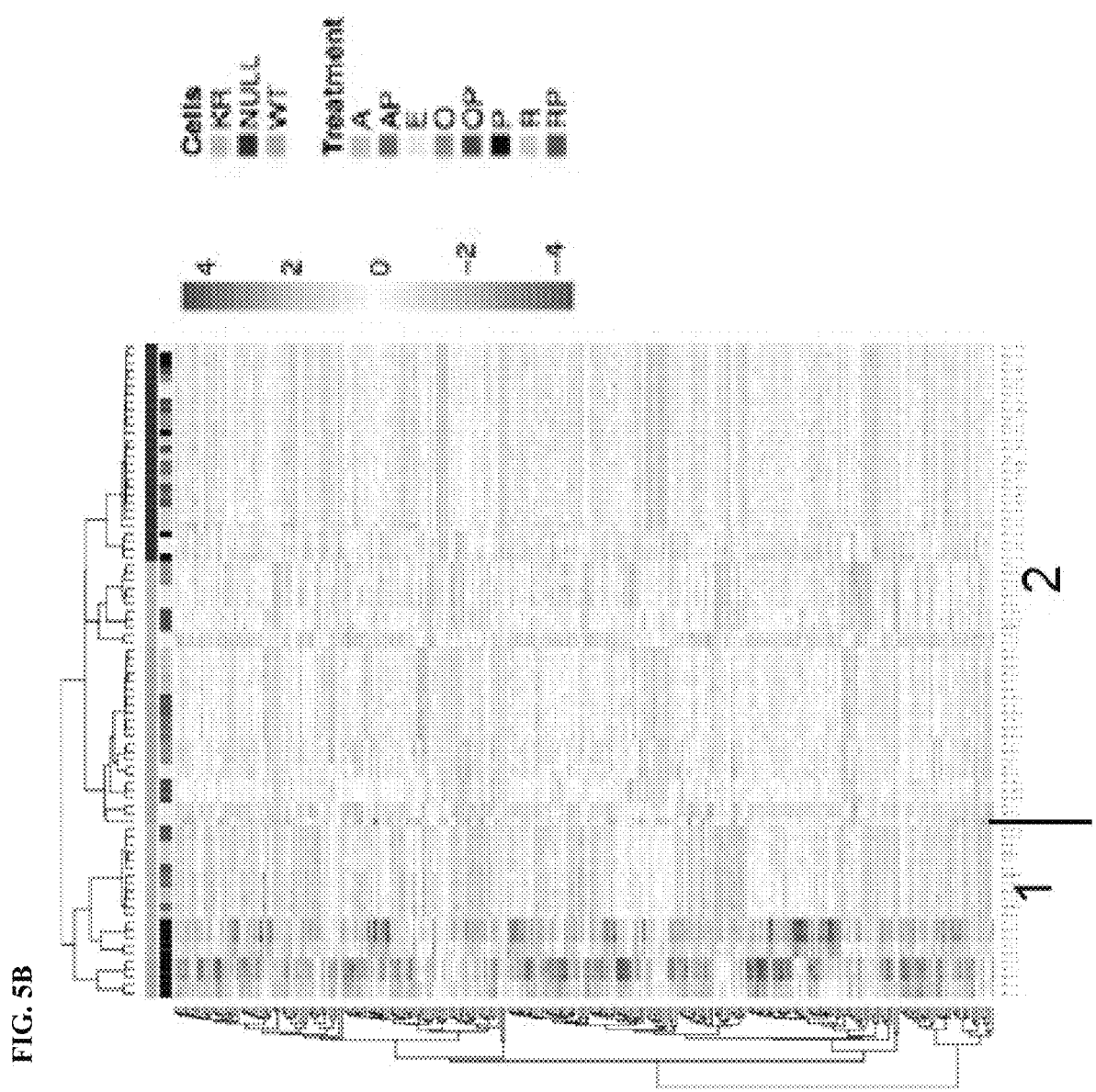
FIG. 5B. Using the full gene expression dataset, multiple sample comparisons (i.e. vehicle vs. P) were made and genes that were significantly regulated were isolated (rows). These genes were clustered via unsupervised hierarchal clustering methods and two major branches were identified (cluster 1 and 2). In addition, sub-branches can also be seen, suggesting a total of five independent sample groups.

In addition to unsupervised NMF clustering (above), differential gene expression analysis between various biologically interesting cell line/treatment comparisons were performed and 251 genes that were up- or down-regulated greater than two-fold in any comparison were identified (FIG. 5B). Using this set of PR regulated genes, unsupervised hierarchal clustering revealed that progestin-treated samples clustered closely together in cells expressing either WT or KR. Hierarchical clustering revealed two major branches of closely related samples: (1) WT cells treated with progestin and KR cells treated with progestin, mifepristone, or aglepristone, and (2) WT cells treated with any antiprogestin or vehicle, KR cells treated with onapristone or vehicle, and all PR-null cells regardless of treatment (FIG. 5B). This result demonstrates that various antiprogestins have different transcriptional effects depending on the dominant PR species. However, based on this clustering analysis, all samples (expressing WT or KR PR) treated with onapristone were closely related (and members of the second branch), suggesting that onapristone effectively inhibited PR (either WT or KR) transcriptional activity comparable to the level found in PR-null (control) cells (FIG. 5B, cluster 2, right). Furthermore, importantly, onapristone did not stimulate SUMO-deficient PR target gene expression in KR-containing T47D cells, as did mifepristone and aglepristone (FIG. 5B, cluster 1).

Figure 5D:
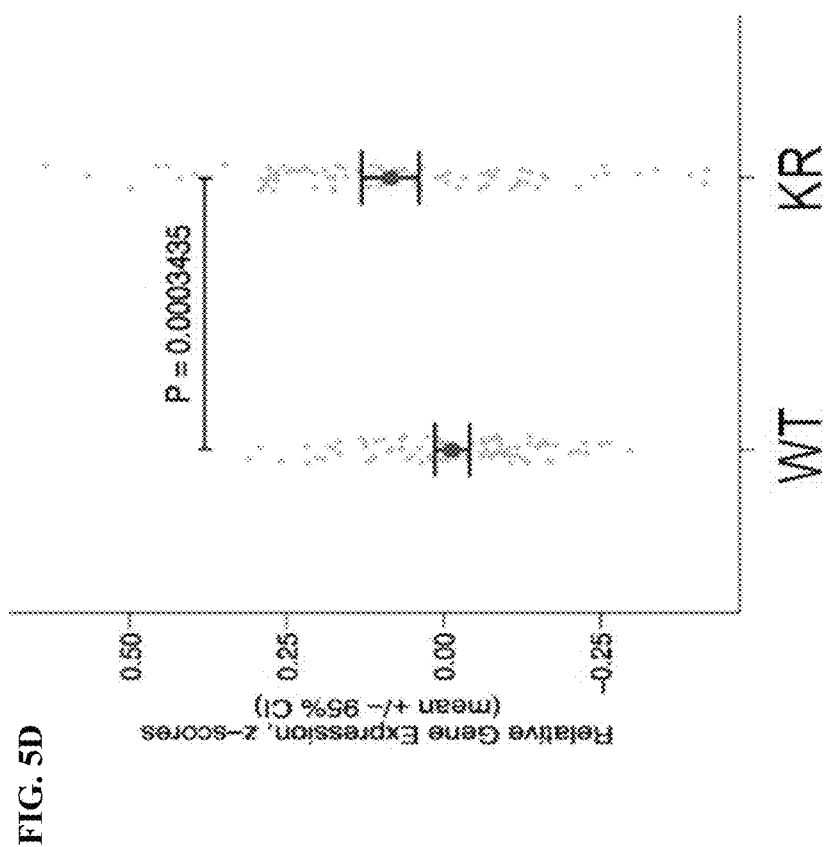
FIG. 5D. The average expression of these 16 genes or 101 genes was compared to the published TCGA breast cancer cohort of PR-negative tumors. Despite all of these tumors being PR-negative (by clinical IHC diagnosis), the "activated PR" target genes (KR) are expressed at significantly higher levels compared to genes upregulated by WT PR (P=0.0003435).
Figure 5C:
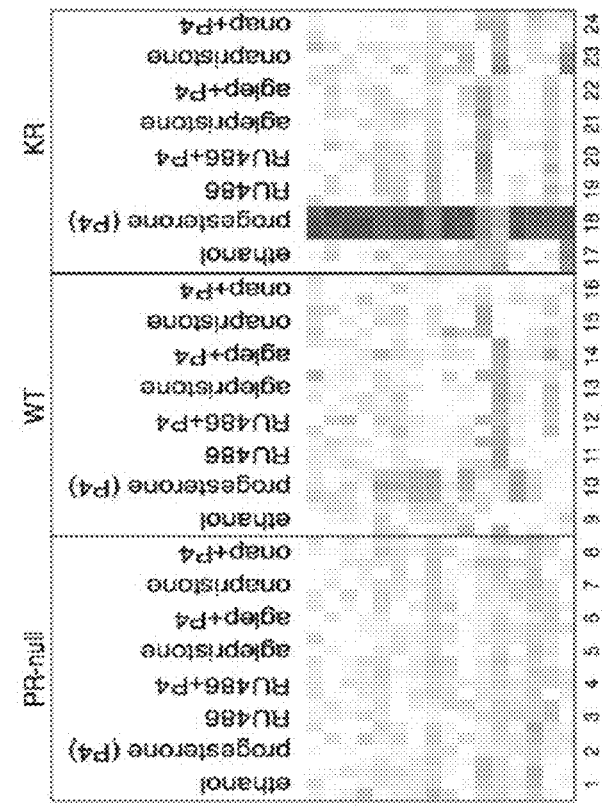
FIG. 5C. 16 PR target genes were identified that were specifically regulated in T47D breast cancer cells expressing Ser294 phosphorylated/SUMO-deficient PR (KR) and not regulated by WT PR (that is not phosphorylated and SUMOylated). In addition, 101 genes were identified that were specifically upregulated by WT PR (non-phosphorylated and SUMOylated PR).
Figure 6B:
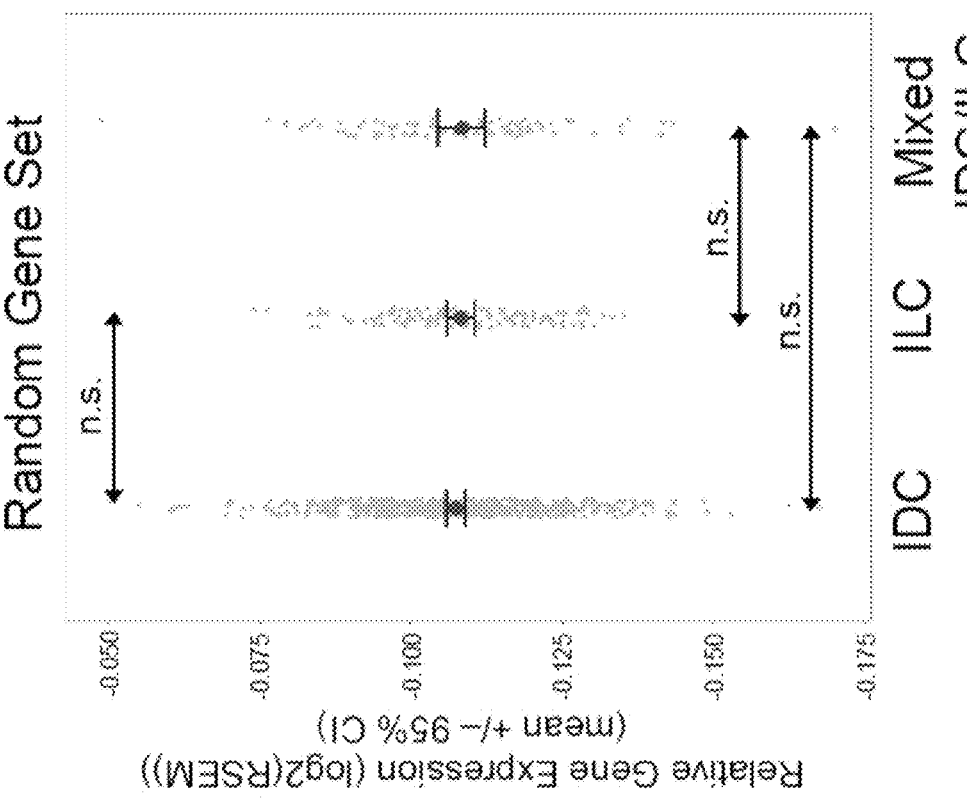
FIG. 6B. A control analysis was repeated with a random set of 150 genes.
Figure 6A:
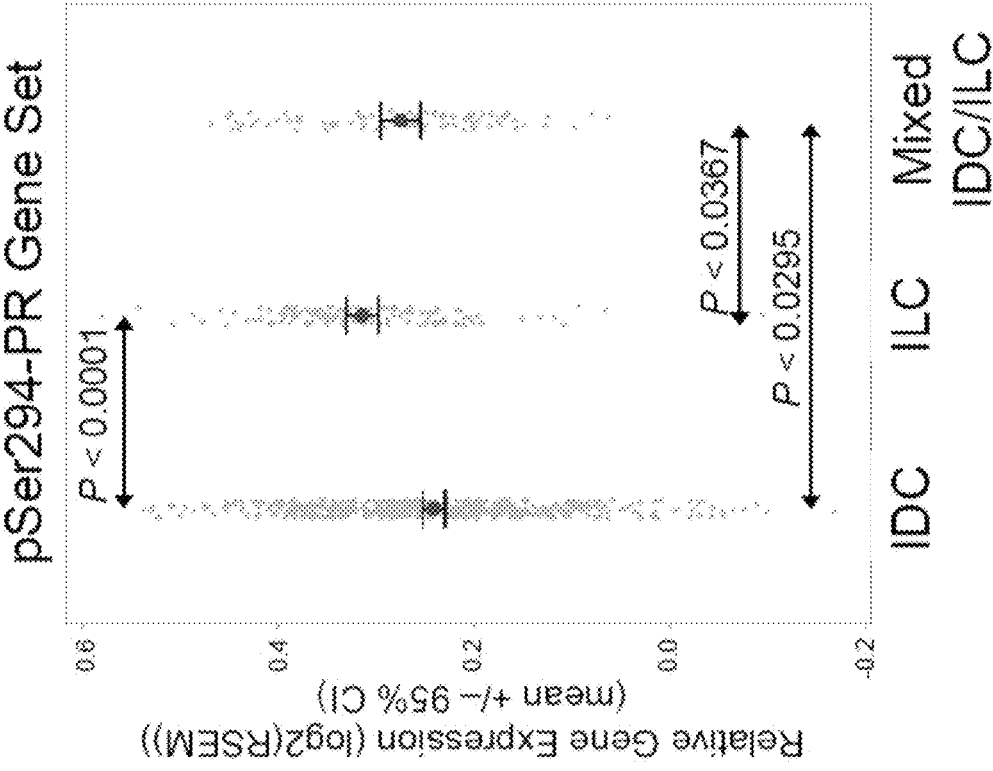
FIG. 6A. Mean gene expression values for a phospho-Ser294 PR gene set (see FIG. 2C) were plotted (grey dots) for tumors classified as invasive ductal carcinoma (IDC), ILC, or mixed IDC/ILC by the TCGA project. The mean of all values within each tumor subset were plotted (black dots, −/+95% CI) and groups were statistically compared using an ANOVA with TukeyHSD post-test. Adjusted P values are displayed.

PR-Low (by IHC) Breast Tumors Significantly Express "Activated-PR" Target Gene Signatures PR transcriptional activity is directly linked to rapid proteasome-mediated turnover of ligand-bound receptors (Lange et al. *Proc Natl Acad Sci USA* 2000, 97:1032-1037; Shen et al. *Mol Cell Biol* 2001, 21:6122-6131) and ligand-dependent PR downregulation is greatly augmented by phosphorylation of PR Ser294 in response to activated MAPK or CDK2 signaling pathways [33]. To address this context-dependent complexity, "activated PR" target genes were identified that were specifically regulated in cells expressing SUMO-deficient PRs (as markers of phosphorylated or hyper-activated PR transcriptional activity) and their average expression levels in the TCGA breast cancer patient cohort were examined (Cancer Genome Atlas Network: Comprehensive molecular portraits of human breast tumours. *Nature* 2012, 490:61-70). First, only Luminal A, B and HER2-enriched tumors that were diagnosed as ER+ but PR-negative were isolated by clinical IHC, as it was hypothesized that some of these tumors could contain undetected but hyperactivated PRs. Next, in these the expression of genes known to be primarily upregulated by deSUMOylated (i.e. phosphorylated) activated PRs relative to genes known to be regulated by SUMOylated PRs tumors were compared (FIG. 5C). Tumors clinically classified as PR-negative were characterized by elevated expression of "activated PR" target genes (FIG. 5D). These unexpected results suggest that a cohort of "PR-negative" breast tumors assigned using standard clinical IHC protocols in fact express significantly high levels of phospho-Ser294 PR target gene mRNA transcripts whose collective expression (i.e. the activated PR transcriptome) signifies the presence of activated phospho-Ser294 PRs. These data suggest that modified PRs cannot be reliably detected in the clinical setting by measurement of PR protein expression (as determined by IHC) as the sole marker of PR activity. Indeed, in in the TMA results (above), PR Ser294 phosphorylation and total PR expression were not substantially correlated in individual tumors.

Gene Sets Derived from T47D Cells Expressing WT PR and KR PR

The 16 genes of Table 2 were discovered to be highly upregulated by progestin in cells expressing KR PR, compared to WT PR. These genes were also not regulated by other PR ligands.

The 101 genes of Table 3 were discovered to be highly upregulated by progestin in cells expressing WT PR, compared to KR PR. These genes were also not regulated by other PR ligands.

These gene sets were used in the analysis described in FIG. 5C, D.

TABLE 2

TK16 gene list

SPRYD5
MAP1A
SPINK5L3
THY1
TUBA3D
TUBA3E
UTS2D
PDK4
MSX2
KIAA0513
PHLDA1
KLF9
TSC22D1
KHDRBS3
ATG12
SLC35C1

TABLE 3

T47D_2up gene list

| | | | |
|---|---|---|---|
| FOXO4 | PFKFB3 | LOC653103 | SLC39A14 |
| CCND1 | FAM43A | STMN3 | TIPARP |
| IL20RA | TMEM43 | MAFB | FAM104A |
| FKBP5 | TNFRSF10B | PRKAB2 | C13orf15 |
| CAMSAP1 | EP400 | SEC14L2 | BICD2 |
| SEPT5 | C17orf79 | EGFLAM | TNFRSF21 |
| ACOT6 | RHOU | GRB10 | CMTM7 |
| RBPMS2 | GPR124 | FAM105A | STAT5A |
| VDR | TRAF5 | PPP1R14C | ADARB1 |
| NET1 | CLDN8 | SLC25A18 | NDRG1 |
| MMP25 | ZDHHC14 | SP110 | CA12 |
| ST3GAL1 | SCML1 | CA4 | UTS2D |
| PACSIN1 | RAB11FIP1 | ZMYND19 | SGK |
| LOC642031 | CLCC1 | MAT2A | SGK1 |
| KCNG1 | CLPTM1L | TRK1 | |
| SRGN | C16orf80 | F3 | |
| AXUD1 | NPTX1 | FOXC1 | |
| PHACTR3 | PDXP | EIF4A3 | |
| SLC31A2 | CEBPD | C3orf70 | |
| SEPX1 | MPHOSPH10 | KLF4 | |
| SLC25A25 | C6orf81 | GJB2 | |
| PIM2 | C6orf85 | FAM107B | |
| NFKBIA | SCRN1 | PRICKLE1 | |
| SCRG1 | HSD11B2 | GOLSYN | |
| GOT1 | YTHDF1 | BDNF | |
| KRT73 | RASSF2 | FJX1 | |
| RCAN1 | KBTBD11 | PDK4 | |
| ANKRD11 | ISG20L1 | FHL3 | |
| C11orf75 | TRNP1 | UGCG | |

Phosph-Ser294 PR Target Genes are More Highly Expressed in ILC Tumors Compared to IDC Tumors TMA analysis (FIG. 2D) revealed that phospho-Ser294 PR expression was significantly associated with infiltrating lobular carcinoma (ILC), when compared to other tumor types included in the model. TCGA recently published a comprehensive analysis that directly compared ILC and IDC breast tumors (Ciriello et al. *Cell* 2015, 163:506-519). This large independent tumor cohort was used to further probe the relationship between phospho-Ser294 PR signaling in lobular versus ductal tumors. The expression levels of a phospho-PR gene set in ILC, IDC, and mixed IDC/ILC tumors from the TCGA dataset was compared (FIG. 8A). The phospho-PR gene set (upregulated by phospho-PR/SUMO-deficient PR, FIG. 2C) was significantly more expressed in the ILC tumors, when compared to the IDC and mixed ILC/IDC tumors (P<0.0001, ANOVA with TukeyHSD post-test; n=705). These data suggest that genes regulated by phospho-Ser294 PR may drive cells toward the ILC tumor lineage, as compared to ductal subtypes.

Gene Set Enrichment Analysis (GSEA) Reveals Mechanisms for SUMO-Deficient PR Transcriptional Activation Whole genome expression analysis allows the identification of functional characteristics within a dataset that will lead to new hypotheses about the model system. Notably, complex cellular responses often result from subtle changes in gene expression levels of multiple genes acting in concert to mediate an important biological outcome. Thus, gene set enrichment analysis (GSEA) was employed to identify gene sets significantly enriched by progesterone or in SPRM-treated groups relative to controls and specifically regulated by phospho-Ser294 PRs. All seven gene set collections from the Molecular Signatures Database (MSigDB, version 4) (Subramanian et al. *Proc Natl Acad Sci USA* 2005, 102: 15545-15550) were analyzed independently among pairwise sample/treatment comparisons. Comparisons of data derived from cells expressing SUMO-deficient/phospho-Ser294 mimic (KR) PR to unmodified WT-PR (−/+SPRMs) revealed numerous significant (nominal P<0.05, FDR<0.25) gene sets. In addition to predicted PR target gene sets (FIG. 11A), ERBB2/HER2 was observed as a phospho-Ser294-PR driven gene set (FIG. 11B) as previously described (Knutson et al. *Breast Cancer Res* 2012, 14:R95). In addition, PAX2 and aryl hydrocarbon receptor (AHR) as well as androgen receptor (AR) and glucocorticoid receptor (GR) gene sets (which share similar consensus sequences to PR (Tang et al. A Comprehensive View of Nuclear Receptor Cancer Cistromes. *Cancer Res* 2011)) were significantly upregulated in cells expressing KR-PR (+SPRMs) but not in similarly treated cells expressing WT-PR (FIG. 11C-E), suggesting that genes regulated by active SUMO-deficient or phospho-Ser294 PRs are more likely to contain classical steroid receptor binding motifs near the transcriptional start site and may thus have DNA binding priority relative to unmodified WT PRs (i.e. primarily de-phosphorylated put capable of undergoing ligand-induced SUMOylation). Finally, six significantly enriched EVI-1/RUNX (also called AML) gene sets were observed to be uniquely regulated in cells expressing KR-PR (+SPRMs) relative to cells expressing WT-PR (+SPRMs) (FIG. 11F), suggesting that phosphorylated PRs and RUNX-factors may cooperate on selected target genes. Three RUNX transcription factors have been described and are important mediators in multiple cancers, including AML. Notably, RUNX transcription factors are primarily expressed in stem cells and regulate stem cell renewal (Kataoka et al. *Cancer Sci* 2012, 103:1371-1377.).

Functional Cooperation between Phospho-Ser294 PR and RUNX2

Figure 7A:
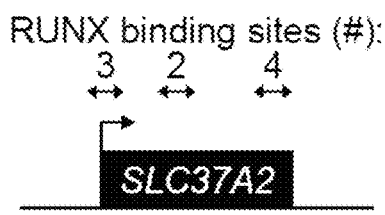
FIG. 7A. SLC37A2 genomic region contains multiple RUNX binding motifs and other regulatory regions (CpG islands and other transcription factor binding hot spots). The number (#) of RUNX binding motifs within three major regions are listed.
Figure 7B:
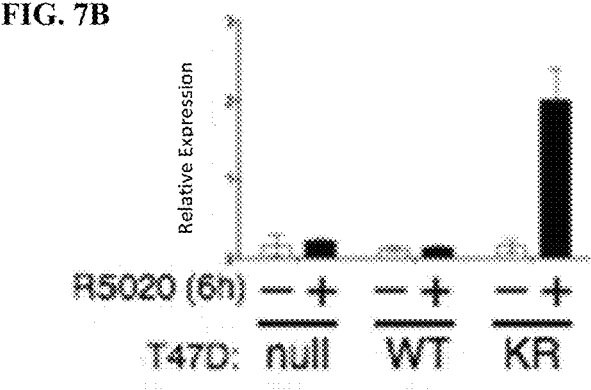
FIG. 7B. SLC37A2 expression in T47D cells was measured after treatment with progestin (R5020) by RT-qPCR.
Figure 7C:
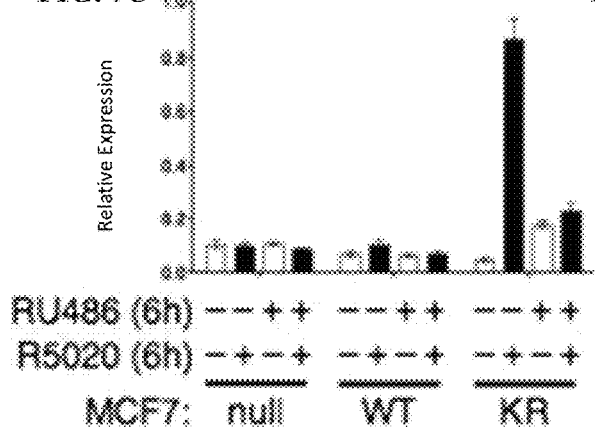
FIG. 7C. SLC37A2 expression in MCF-7 cells was measured after treatment with progestin (R5020) and/or antiprogestin (mifepristone) by RT-qPCR.
Figure 7D:
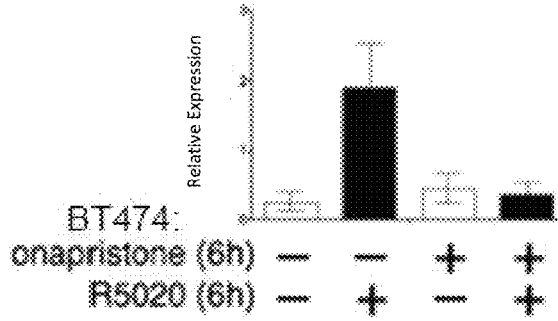
FIG. 7D. SLC37A2 expression in BT474 cells was measured after treatment with progestin (R5020) and/or antiprogestin (onapristone) by RT-qPCR.
Figure 7E:
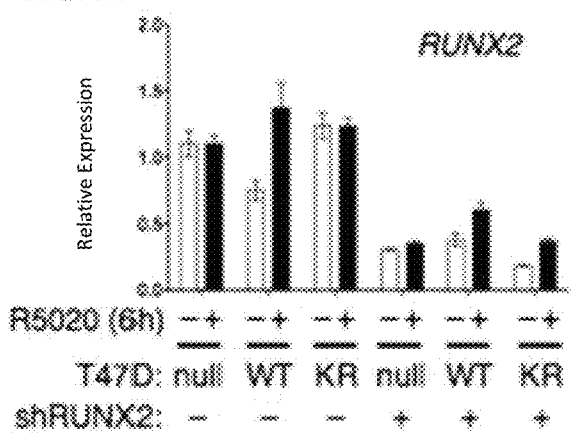
FIG. 7E. T47D cells expressing WT or KR PR were engineered to stably express shRNAs targeting RUNX2, resulting in approximately 50% reduction of RUNX2 mRNA levels.
Figure 7F:
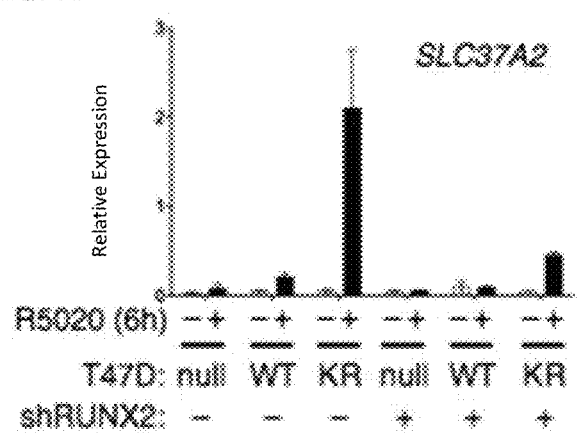
FIG. 7F. In cells stably expressing shRNAs targeting RUNX2, expression of the KR PR target gene SLC37A2 was significantly reduced.

The above gene set enrichment analysis (GSEA) results suggest that SUMO-deficient phospho-Ser294 PRs regulate a set of genes also regulated by RUNX factors. PR cooperation with one or more RUNX factors may be a mechanism for promoter selection by uniquely modified receptors. The family of RUNX transcription factors (RUNX1, 2, and 3) has complex roles in development and tumor formation with both tumor suppressive and tumor-promoting activities. Interestingly, phenotypes associated with RUNX2 expression in mammary epithelial cells closely resemble phenotypes dependent on PR as well as progestin-mediated gene expression (namely cyclin D1 expression, proliferation, luminal progenitor cell maintenance, and alveolar expansion during mammary gland development; see Discussion). From the GSEA results, SLC37A2, a candidate PR target gene containing multiple RUNX2 binding motifs immediately upstream and within the gene, was identified (FIG. 7A). SLC37A2 is a glucose-6-phosphate transporter expressed in monocytes as well as breast and cervical tissues. Although no studies have been conducted in cancer models, SLC37A2 is associated with at least 17 other public data sets that define stem cell genes or proteins (Xu et al. *Database* (*Oxford*) 2013, 2013:bat045). PR/progestin-dependent regulation of SLC37A2 mRNA expression in multiple cell line models was thus measured. In T47D cell models, SLC37A2 expression was robustly stimulated by progestin in cells expressing SUMO-deficient PR, but not in cells expressing WT PR (FIG. 7B). Similarly, in MCF-7 cell line models overexpressing SUMO-deficient K388R PR, SLC37A2 expression was upregulated by progestin exposure but blocked by mifepristone (FIG. 7C). Interestingly, however, as predicted from the gene array studies, mifepristone exhibited weak partial agonist activity in cells expressing KR PRs (compare RU486 treatments across cell lines). BT474 breast cancer cells (luminal B; ER+/PR+/ERBB2+) super-induce selected SUMO-sensitive (activated) PR target genes upon progestin treatment relative to other PR+ cell line models, presumably because kinase pathways downstream of Her2 (i.e. MAPKs) input to persistent PR Ser294 phosphorylation (Knutson et al. *Breast Cancer Res* 2012, 14:R95). In unmodified BT474 cells, progestin exposure resulted in highly phosphorylated PR that turned over rapidly, characteristic of PRs with heightened transcriptional activity (Shen et al. *Mol Cell Biol* 2001, 21:6122-6131). In these cells, progestin treatment also stimulated robust SLC37A2 mRNA expression that was effectively blocked by treatment with onapristone (FIG. 7D). The requirement for RUNX2 expression in transcriptional responses to progestin was tested by knocking down RUNX2 in T47D cells using shRNAs. Although T47D cells remained relatively resistant to RUNX2 loss, RUNX2 expression was reproducibly reduced by approximately 50% upon expression of specific shRNAs relative to shRNA controls (FIG. 7E). Knockdown of RUNX2 greatly attenuated induction of SLC37A2 expression in cells expressing KR-PR and treated with progestin relative to controls (FIG. 7D). These data demonstrate that PR cooperation with RUNX2 contributes to SLC37A2 expression as part of a unique phospho-Ser294 PR transcriptome in breast cancer cells and illustrate the impact of context-dependent cell signaling on PR actions.

PR Ser294 Phosphorylation is Required for Formation of Secondary Mammospheres

HER2, PAX2, AHR, AR, and RUNX factors have each been implicated in cancer stem cell biology (Hosseini et al. *Nature* 2016, 540:552-558; Kataoka et al. Cancer Sci 2012, 103:1371-1377; Li C G, et al.; Casado et al. *Stem Cells Int* 2016, 2016:4389802 *Front Genet* 2012, 3:6; Davies et al. *Stem Cells Int* 2016, 2016:4829602). Further these factors may cooperate; for example, AR/RUNX2 complexes are important drivers of prostate cancer stem cell expansion (Baniwal et al. *J Cell Physiol* 2012, 227:2276-2282). Mammosphere assays provide an assay of stem cell potential, wherein formation of secondary mammospheres (i.e. derived from dissociated and serially passaged primary mammospheres) is a definitive assay of the ability of minority breast cancer cell stem cells within a heterogeneous population to expand and reestablish as E-cadherin positive spheres able to grow in suspension culture following long-term serial passage as non-adherent cells (Grimshaw et al. *Breast Cancer Res* 2008, 10:R52). To demonstrate a role for phosphorylated PRs in breast cancer stem cell biology, mammosphere assays were performed using T47D cell model systems expressing either empty vector (EV PR-null), unmodified WT PR-B, point mutant KR PR-B (K388R), or point mutant S294A PR-B missing the consensus MAPK phosphorylation site Ser residue (FIG. 8). Equal numbers of T47D cells were inoculated into primary mammosphere assays (i.e. suspended cell culture) in defined media and mammosphere numbers were scored after 2 weeks by manual counting using a uniformly scaled grid; primary mammospheres were gently dissociated and reseeded in order to form secondary mammospheres (see Methods). Interestingly, cells expressing either empty vector (EV) or WT PR produced similar basal numbers of primary (~25) and secondary (~10) mammospheres, while cells expressing KR (phospho-mimic) PR consistently produced 55-70 primary mammospheres and 35-50 secondary mammospheres (FIG. 8A, B). Surprisingly, both primary and secondary mammosphere formation was greatly attenuated in cells expressing S294A PR relative to controls and cells expressing KR PR. Interestingly, PR-null (vector control) cells formed small "flat" or "non-spheroid" clumps of loosely-associated cells with raged or rough edges relative to cells expressing wt PR-B, which formed small round and smooth mammospheres (FIG. 8C). Notably, cells expressing KR PR formed larger mammospheres relative to cells expressing WT PR, in sharp contrast to cells expressing S294A PR, which formed few very small mammospheres (FIG. 8C). Addition of either estrogen (1 nM) or progesterone (10 nM; shown) to mammosphere culture media had no significant effect on total numbers in any condition. However, removal (and add-back) of EGF to the mammosphere culture media demonstrated a clear requirement for growth factor signaling (FIGS. 8D, E). These data suggest that formation of secondary mammospheres, a definitive assay of stem cell outgrowth, is largely dependent on the presence of signaling inputs (EGF) to phospho-Ser294 PRs in T47D breast cancer cells but does not require exogenously added progesterone. Further, the finding that expression of S294A PR attenuated mammosphere formation to levels below that of either PR-null or WT PR-containing cells in EGF-containing media suggests a dominant negative effect of this mutant receptor, perhaps via interaction with other steroid receptors such as ER or AR (see Discussion). In a similar set of experiments, the ability of PR-B+T47D cells stably expressing either control shRNA (shGFP) or RUNX2 shRNA to form mammospheres was tested (FIG. 8F-G). Again, cells expressing K388R PR-B formed larger and significantly greater numbers of primary mammospheres relative to cells expressing unmodified (WT) PR-B. Knockdown of RUNX2 greatly attenuated the formation of primary mammospheres in T47D cells expressing either WT PR-B or K388R PR-B, rendering the assay of secondary mammospheres infeasible.

Figure 9A:
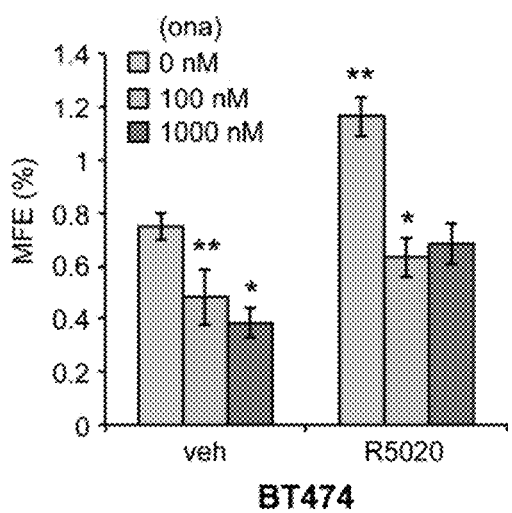
FIG. 9A. Primary mammospheres in HER2+BT474 cells expressing endogenous estrogen receptor (ER) and progesterone receptor isoforms (PR-A and PR-B) plotted as a percentage of Mammosphere Forming Efficiency (MFE; see Methods). Cells were treated with vehicle (EtOH) control or R5020 (10 nM) without or with increasing concentrations of the type II antipristone, onapristone (0, 100, or 1000 nM). Data is represented as the average±SD of three readings. *p<0.05, p<0.01, *p<0.001 compared to vehicle control. Secondary mammospheres failed to form in onapristone-containing media.
Figure 9B:
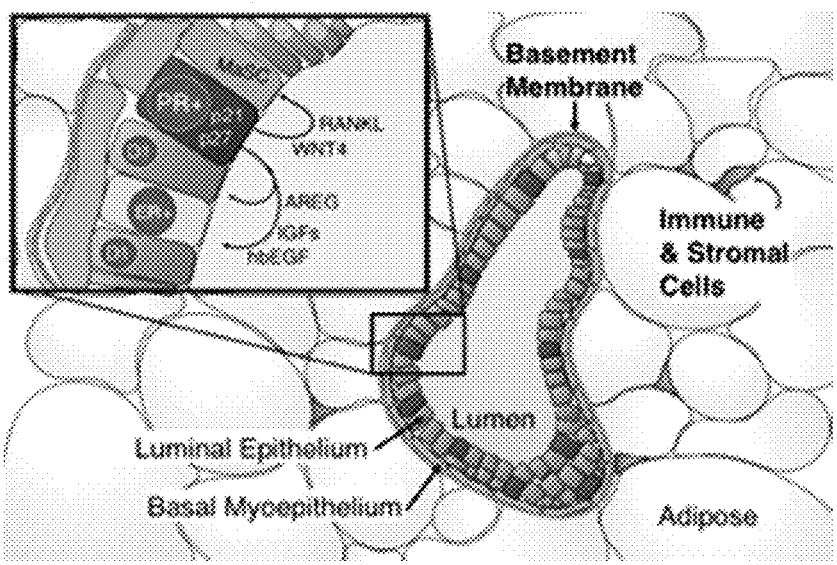
FIG. 9(A-C) shows Primary Mammosphere Formation in Unmodified HER2+BT474 Breast Cancer Cells.
Figure 9C:
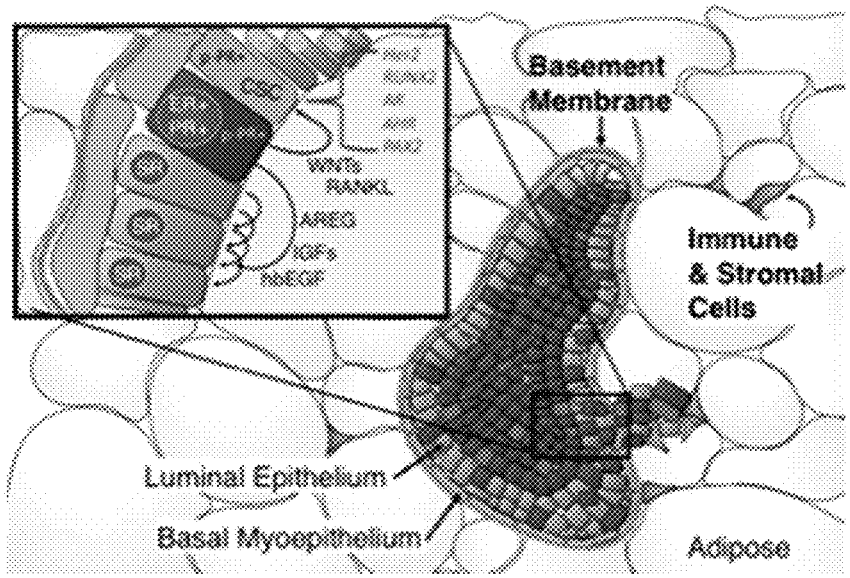

The results were also validated in unmodified ER+/PR+ BT474 cells. These cells express high levels of activated Her2 and thus more closely resemble luminal B type breast cancers, but express endogenous ER and both PR isoforms (PR-A and PR-B). In this "high-kinase" context, PRs are readily phosphorylated on Ser294. Notably, BT474 cells exhibited a relatively high level of basal primary mammosphere formation that was further elevated in the presence of progestin (FIG. 9A). Treatment with onapristone (an antiprogestin that blocks PR Ser294 phosphorylation), effectively reduced both basal and progestin-stimulated primary mammosphere formation. As with RUNX2 knock-down studies, secondary mammospheres failed to form in the presence of onapri stone.

Collectively, these data suggest that phospho-PRs are key "gate-keepers" that enable breast tumor progression via induction of multiple signaling pathways, including those required for outgrowth of breast cancer stem or progenitor cells. Identification of phosphorylated receptors in human tumors and discovery of phospho-PR-regulated pathways (i.e. including RUNX2) suggests novel ways to specifically target breast cancer stem cell outgrowth as part of durable breast cancer therapies.

Discussion

The data described herein provide insight into how progestin treatment may block proliferation in some strongly ER+/PR+ breast cancers (containing PRs capable of undergoing regulated SUMOylation, a modification that is primarily transcriptionally repressive at SR target genes and required to repress ER-alpha and other SR-dependent transcriptional events), while stimulating proliferation in others (containing modest levels of phosphorylated and SUMO-deficient PRs that are active drivers of unique cancer transcriptomes). Additionally, these findings implicate PR as a master regulator of cell fate of both normal mammary epithelial and cancer stem/progenitor cell populations and reveal a key role for Ser294 phosphorylated PRs in this aspect of PR-driven cell biology. Ultimately, the transcriptional activity and biological actions of PRs are profoundly influenced by context. Herein, a subset of PR target genes were identified that can be used as biomarkers reflective of "activated" PR expression (i.e. independently of clinically derived PR status as defined by IHC-based methods). Using breast cancer mRNA expression data from the TCGA project, activated PR target genes were determined to be significantly upregulated in ILC as well as clinically determined "PR-negative" luminal patient samples (compared to gene sets specifically regulated by inactive or stabilized and abundant receptors). These data suggest that a subset of breast cancer patients whose tumors are clinically classified as PR-negative may have cancers driven in part by modest levels of highly transcriptionally active PRs that go undetected by clinical standards. Alternatively, abundant phospho-PRs may reside in minority cancer cell populations or "PR+ islands" within largely PR-null tumors (FIGS. 1-2) capable of early dissemination (Hosseini et al. *Nature* 2016, 540:552-558). Patients harboring such tumors are strong candidates for antiprogestin therapy, including onapristone or similar agents that block PR Ser294 phosphorylation.

As an ER target gene product, PR is classically used as a biomarker of functional ER and thus indicative of a high likelihood of response to ER-targeted endocrine therapies (Bentzon et al. 2008, *International Journal of Cancer* 122: 1089-1094; Prat et al. *Journal of Clinical Oncology* 2013, 31:203-209). Tumors defined as ER+PR+ HER2− are usually less aggressive and classified within the luminal A or B subtypes. Of these, ER+/PR-low or null tumors (i.e. luminal B subtype) are more likely to become endocrine resistant. The presence of PR can profoundly modify ER behavior and cellular responses to estrogen, in part by direct ER/PR interactions (Mohammed et al. *Nature* 2015, 523:313-317; Ballare et al. *Mol Cell Biol* 2003, 23:1994-2008). Modest levels of PR-B, but not progesterone, were required for estrogen-induced changes in global gene expression associated with breast tumor progression to endocrine resistance and poor disease outcome (Daniel et al. *Oncogene* 2015, 34:506-515). In contrast, estrogenic responses were inhibited when ER+/PR+ breast cancer cells and breast tumor explants were exposed to both hormones, however relatively high hormone concentrations were used to demonstrate these effects (Mohammed et al. *Nature* 2015, 523:313-317; Singhal et al. *Sci Adv* 2016, 2:e1501924). Like estrogen (alone), progesterone (alone) is a potent driver of breast cancer cell proliferation (FIG. 3A). PR+ but ER-null mammary gland progenitor cells exist, suggesting unique roles for PR that are independent of ER; PR+ bipotent progenitor cells are estrogen-insensitive, while estrogen regulates PR expression only in mature luminal cells (Hilton et al. *Mol Cell Endocrinol* 2012, 361:191-201). Progesterone but not estrogen has emerged as a key mediator of both normal and neoplastic mammary gland stem cell expansion (Tanos et al.; *Science translational medicine* 2013, 5:182ra155; Schramek et al. *Nature* 2010, 468:98-102; Joshi et al. *Nature* 2010, 465:803-807; Asselin-Labat et al. *Nature* 2010, 465:798-802). The studies described herein strongly implicate Ser294 phosphorylated PRs in this activity (FIG. 8). The finding that PR Ser294 phosphorylation is widely observed in breast tumors and is primarily found in premalignant regions suggests that this modification of PR is a relatively early event in tumor progression. Notably, expression of the PR target gene, RANKL, also primarily occurs in early-stage pre-malignant epithelial layers (i.e. DCIS, and normal-like regions) (Tanos et al.; *Science translational medicine* 2013, 5:182ra155; Brisken, *Nat Rev Cancer* 2013, 13:385-396).

Commonly used PR ligands (agonists and antagonists alike) were found to induce PR Ser294 phosphorylation and phospho-PR target gene expression (FIGS. 4-5). Indeed, the partial agonist activity of antiprogestins appears to map to SUMO-deficient/phosphorylated receptors. Only onapristone was effective in blocking Ser294 phosphorylation and gene expression in cells expressing either wild type (WT) PR or SUMO-deficient (KR) PR (FIGS. 4-5). In breast cancer cells expressing KR PR, mifepristone and aglepristone stimulated considerable Ser294 phosphorylation and gene regulation suggesting these antagonists may be less effective in cells that contain the highly transcriptionally active deSUMOylated PR. Antiprogestin therapies are being actively studied for breast (and other) cancers, therefore, a more comprehensive understanding of the differences in transcriptional regulation by these ligands (in relation to PR post-translational modifications) will be critical. The data described herein (see, e.g., FIG. 5) demonstrate that different antiprogestins have unique gene regulatory action depending on the status of PR post-translational modifications. Both mifepristone and progestin agonists (progesterone or R5020) upregulated similar genes in cells expressing SUMO-deficient (phospho-mimic) PRs, suggesting that mifepristone is a poor antiprogestin in that context. However, mifepristone treatment of cells containing WT PR (capable of SUMOylation) was far less likely to stimulate the expression of progestin-regulated PR target genes, making it a useful antagonist in that context. These results suggest that successful therapies for breast cancer patients using antiprogestins should consider the status of PR post-translational events. These data may explain why mifepristone (RU486) has not been successful in clinical trials for breast cancer, considering that the TMA revealed that PRs in a majority of breast tumors are phosphorylated on Ser294, a posttranslational event predicted to confer partial agonist activity to ligands of this class. As such, alternative antiprogestin therapies (i.e. onapristone or SPRMs that block PR Ser294 phosphorylation) may be more successful to silence the transcriptional action of activated phospho-PRs.

Herein, gene set enrichment analysis (GSEA) analyses confirmed that phospho-PRs significantly induce expression of Her2-associated gene sets and demonstrated that phospho-PR target genes also include key mediators of cancer stem cell biology, including PAX, AHR, AR, and RUNX family members (FIGS. 7, 10). SUMO-deficient or phospho-Ser294 PR target genes may be co-regulated by one or more of these transcription factor families. Notably, PAX2 is overexpressed in >50% of breast cancers and was required for progesterone-stimulated lateral side-branching and lobular development in a murine Pax2-knockout model (Silberstein et al. *Oncogene* 2002, 21:1009-1016). Pax2 knockout in murine mammary glands phenotypically resembled PR or Wnt4 knockout mice (Brisken et al. *Proc Natl Acad Sci USA* 1998, 95:5076-5081; Brisken et al. *Genes Dev* 2000, 14:650-654). These data indicate that PR-driven pathways important during mammary gland development may remain active during breast tumor progression. Aryl hydrocarbon receptor (AHR) is a transcription factor member of the nuclear receptor (NR) superfamily expressed in female reproductive tissues that interacts with multiple environmental toxins as ligands, resulting in AHR translocation to the nucleus where it dimerizes with AHR-nuclear translocator (ARNT). This triggers upregulated expression of cytochrome P450 enzymes that help metabolize a variety of compounds. Environmental toxins can modulate reproductive functions and alter homeostasis of many endocrine functions in the reproductive tract largely because ligand-activated AHR can interfere with SR signaling. Thus, AHR is known to disrupt ER and AR target gene expression (Ohtake et al. *J Steroid Biochem Mol Biol* 2011, 127:102-107). For example, ligand-bound AHR/ARNT binds specific motifs positioned near ER binding motifs in the promoters of multiple ER target genes, disrupting ER-mediated transcription (Elbi et al. *Mol Biol Cell* 2002, 13:2001-2015; Pocar et al. *Reproduction* 2005, 129:379-389). Similarly, the GSEA results demonstrate that activated PRs drive expression of important SR regulated target genes that can also be disrupted by AHR/ARNT complexes (FIG. 11). Thus, phosphorylated and SUMO-deficient PR may interact preferentially with AHR/ARNT repressed genes.

Six significantly enriched EVI1 or RUNX (also called AML) gene sets were observed to be regulated in cells expressing KR-PR+progestin, compared to cells expressing WT-PR+progestin (FIG. 11). EVI1 is a transcription factor that is primarily expressed in stem cells and regulates stem cell renewal. The oncoprotein is well studied in acute myeloid leukemia (AML) and when highly expressed, confers poor outcome. AML is primarily caused by gene translocations between strong promoters and the ecotropic viral integration site 1 (EVI1) and runt-related transcription factor 1 (RUNX1) genes. Three RUNX transcription factors have been described and are important mediators in multiple cancers in addition to AML. In particular, the GSEA results demonstrate that SUMO-deficient phospho-PR regulates a set of genes that contain RUNX DNA binding motifs in their promoters, suggesting that SUMO-deficient or phosphorylated PR and RUNX-factors may cooperate in a way that WT PR (i.e. SUMOylated) does not. Both RUNX1 and RUNX3 have tumor suppressor roles in breast cancers, while RUNX2 is tumor promoting. A requirement for RUNX2 in phospho-Ser294 PR target gene regulation (i.e. using the SLC37A2 gene identified in the arrays; FIG. 7) as well as in primary mammosphere formation (FIG. 8) was validated. RUNX2 interacts with estrogen rector (ER), androgen receptor (AR), and the glucocorticoid receptor (GR) to facilitate steroid hormone mediated transcriptional activity. Curiously, we were unable to co-immunoprecipitate RUNX2 and PR from breast cancer cell whole cell lysates or detect them as co-associated factors at progesterone response element (PRE) sites by ChIP assays, suggesting that these factors function in the same pathway but may interact indirectly or may associate transiently or successively via binding to separate or distant sites in chromatin.

The data reported herein show that RUNX2 is essential for mammosphere formation in PR-B+ cells (FIG. 8). Interestingly, while mammosphere formation was insensitive to added hormones, EGF was required for spheroid formation in breast cancer cells expressing K388R (phospho-mimic) PRs (FIG. 8D-E). These data suggest that cells growing in suspension no longer require exogenously added hormones but instead rely on growth factors to cue context-dependent (i.e. MAPK-dependent) phospho-PR actions, including gene expression of RUNX2. EGF-induced steroid hormone biosynthesis is a topic of further study as a potential mechanism of SR action in breast cancer spheroids carried in media lacking exogenously added hormones (FIG. 8).

In sum, PR is emerging as a major mechanistic player that mediates early breast tumor progression in part via "feeding" the stem cell compartment (i.e. via paracrine signals); the data described herein support a requirement for phosphorylation of PR Ser294 in this activity as an important gatekeeper of breast cancer cell fate and expanded tumor heterogeneity. Most notably, in addition to strongly ER+/PR+ lobular breast cancers, expression of KR specific target genes in human breast tumors clinically determined to be PR-negative was observed. This PR signature is expected to be an important biological "marker" of activated phospho-PR species that undergo rapid protein loss due to turnover, an event that may precede loss of PR mRNA expression in more advanced and strongly Her2+ tumors (Daniel et al. *Mol Endocrinol* 2007, 21:2890-2906; Knutson et al. *Breast Cancer Res* 2012, 14:R95; Lange et al. *Proc Natl Acad Sci USA* 2000, 97:1032-1037). Previous clinical trials using antiprogestins demonstrated poor response rates in PR+ tumors. These agents may have stimulated PR phosphorylation and unwanted target gene expression. Additionally, these early trials primarily targeted PR in strongly ER+/PR+(luminal A) tumors. While this targeting was a logical approach based on high expression of PR protein as a biomarker, the studies described herein suggest a far more complex scenario in which luminal B (PR low) patients are the correct cohort for antiprogestins. The recent finding that PR and Her2, a primary pathway induced by phospho-Ser294 PR (Knutson et al. *Breast Cancer Res* 2012, 14:R95), were requisite mediators of early breast cancer dissemination and metastasis (Hosseini et al. *Nature* 2016, 540:552-558) underscores the relevance. Clearly, a paradigm shift to "activated PR" as measured by the presence of phospho-PR species or phospho-PR target gene sets (in addition to Her2) is needed.

Example 2

Table 4 shows 16 genes that are upregulated in cells expressing high phospho-Ser294 PR compared to cells containing wild type PR, as described in Example 1, and an exemplary probe sequence for each gene. Probing for the upregulation of one, two, three, four, five, six, or more of these genes may be used to validate and/or verify an anti-PR-phospho-Ser294 antibody. Additionally or alternatively, upregulation of one, two, three, four, five, six, or more of these genes may be used to detect high phospho-Ser294 PR in a patient sample.

Tables 5-10 show genes, derived from the Gene Set Enrichment Analysis of Example 1 (see, for example, FIG. 11), the expression of which is altered in cells containing high-phospho-Ser294 PR expression (e.g., K388R cells) compared to cells containing wild type PR, as described in Example 1.

Table 5A shows genes upregulated in cells containing high-phospho-Ser294 expression (e.g., K388R cells); Table 5B shows genes downregulated in cells containing high-phospho-Ser294 expression. The genes in Table 5 are believed to be regulated by the gene for progesterone receptor PGR).

Table 6A shows genes upregulated in cells containing high-phospho-Ser294 expression (e.g., K388R cells); Table 6B shows genes downregulated in cells containing high-phospho-Ser294 expression. The genes in Table 6 are believed to be regulated by the gene for androgen receptor (AR).

Table 7A shows genes upregulated in cells containing high-phospho-Ser294 expression (e.g., K388R cells); Table 7B shows genes downregulated in cells containing high-phospho-Ser294 expression. The genes in Table 7 are believed to be regulated by the paired box (PAX) gene.

Table 8A shows genes upregulated in cells containing high-phospho-Ser294 expression (e.g., K388R cells); Table 8B shows genes downregulated in cells containing high-phospho-Ser294 expression. The genes in Table 8 are believed to be regulated by the gene for aryl hydrocarbon receptor (AHR).

Table 9A shows genes upregulated in cells containing high-phospho-Ser294 expression (e.g., K388R cells); Table 9B shows genes downregulated in cells containing high-phospho-Ser294 expression. The genes in Table 9 are believed to be regulated by the gene for Runt-related transcription factor 1 (RUNX also known as AML).

Table 10A shows genes upregulated in cells containing high-phospho-Ser294 expression (e.g., K388R cells); Table 10B shows genes downregulated in cells containing high-phospho-Ser294 expression. The genes in Table 10 are believed to be regulated by the gene for Erb-B2 Receptor Tyrosine Kinase 2 (ERBB2).

TABLE 4

| Probe_ID | Ref_seq | Probe_Sequence | Symbol | Description |
| --- | --- | --- | --- | --- |
| ILMN_1779875 | NM_006288.2 | CTGAGGCAAGCCATGGAGTGAGACC CAGGAGCCGGACACTTCTCAGGAAA (SEQ ID NO: 1) | THY1 | Homo sapiens Thy-1 cell surface antigen (THY1), mRNA. |
| ILMN_1778523 | NM_001206.2 | GCCCTTCACCATTGTGGAATGATGC CCTGGCTTTAAGGTTTAGCTCCACA (SEQ ID NO: 2) | KLF9 | Homo sapiens Kruppel-like factor 9 (KLF9), mRNA. |
| ILMN_1697543 | NM_001040129.2 | GCAGACTGCCCCAATGTGACAGCAC CTGTTTGTGCCTCAAATGGCCACAC (SEQ ID NO: 3) | SPINK5L3 | Homo sapiens serine protease inhibitor Kazal-type 5-like 3 (SPINK5L3), mRNA. |
| ILMN_1687978 | NM_007350.3 | AACAGTCTCTCCGCCCCGCACCAGA TCAAGTAGTTTGGACATCACCCTAC (SEQ ID NO: 4) | PHLDA1 | Homo sapiens pleckstrin homology-like domain, family A, member 1 (PHLDA1), mRNA. |
| ILMN_1701558 | NM_002373.4 | CCCAAGCAAGCCAGTGAGCAGCCCT GCCAGACTACTGCCAGACTGAGAAA (SEQ ID NO: 5) | MAP1A | Homo sapiens microtubule-associated protein 1A (MAP1A), mRNA. |
| ILMN_1753648 | NM_032681.1 | TCCCTGATATACACCATCCCCAATT GCTCCTTCTCACCTCCTCTCAGGCC (SEQ ID NO: 6) | SPRYD5 | Homo sapiens SPRY domain containing 5 (SPRYD5), mRNA. |
| ILMN_2188204 | NM_004707.2 | GAGTCGTGATTGTACCACTGCATTC CTGCTGAGCAACAGAGTGAGACCCC (SEQ ID NO: 7) | ATG12 | Homo sapiens ATG12 autophagy related 12 homolog (S. cerevisiae) (ATG12), mRNA. |
| ILMN_1684982 | NM_002612.3 | CAGAAGTCCTAGACAGTGACATTTC TTAATGGTGGGAGTCCAGCTCATGC (SEQ ID NO: 8) | PDK4 | Homo sapiens pyruvate dehydrogenase kinase, isozyme 4 (PDK4), mRNA. |
| ILMN_1766951 | NM_002449.4 | AGGTACATTCATCCTCACAGATTGC AAAGGTGATTTGGGTGGGGGTTTAG (SEQ ID NO: 9) | MSX2 | Homo sapiens msh homeobox 2 (MSX2), mRNA. |
| ILMN_1652464 | NM_207312.1 | GGTCCCCAAAGACGTCAATGCGGCC ATCGCCACCATCAAGACCAAGCGCA (SEQ ID NO: 10) | TUBA3E | Homo sapiens tubulin, alpha 3e (TUBA3E), mRNA. |

TABLE 4-continued

| Probe_ID | Ref_seq | Probe_Sequence | Symbol | Description |
|---|---|---|---|---|
| ILMN_1692177 | NM_006022.2 | TCCCAATGGTGTAGACCAGTGGCGATGGATCTAGGAGTTTACCAACTGAG (SEQ ID NO: 11) | TSC22D1 | Homo sapiens TSC22 domain family, member 1 (TSC22D1), transcript variant 2, mRNA. |
| ILMN_2215639 | NM_080386.1 | TCCCCTGCCACCCCCGGGATGGCTGCTTCCAAGTTGTTTGCAATTAAAGG (SEQ ID NO: 12) | TUBA3D | Homo sapiens tubulin, alpha 3d (TUBA3D), mRNA. |
| ILMN_1691747 | NM_006558.1 | AGGCACCTTCAGCGAGGACAGCAAAGGGCGTCTACAGAGACCAGCCATAT (SEQ ID NO: 13) | KHDRBS3 | Homo sapiens KH domain containing, RNA binding, signal transduction associated 3 (KHDRBS3), mRNA. |
| ILMN_2180232 | NM_198152.2 | GCTGGTATATCCAGTGCATTGTTGGCACCATGGGACCAGAAGGTGGTGAC (SEQ ID NO: 14) | UTS2D | Homo sapiens urotensin 2 domain containing (UTS2D), mRNA. |
| ILMN_1680104 | NM_018389.3 | AGGGTGGCTTGCAGTCCCTGGCCCTTCTGGTGGGCATTTGGTATGTCCTT (SEQ ID NO: 15) | SLC35C1 | Homo sapiens solute carrier family 35, member C1 (SLC35C1), mRNA. |
| ILMN_1693233 | NM_014732.2 | CTTCTTGAACCTGGTGGCCCCCGTTGGAACTATCAGTGGCGTCTCCCATG (SEQ ID NO: 16) | KIAA0513 | Homo sapiens KIAA0513 (KIAA0513), mRNA. |

TABLE 5B (PGR_genes_dn)

KLHL5
SPTBN1
OPN3
CCDC126
CXCL14
PHC2
GRB2
RERE
ETS1
DOLPP1
CDKN1A
JPH1

TABLE 5A (PGR_genes_up)

ZMYND8
ELF5
SMOX
CD36
UVRAG
MBP
CPEB4
BCL6
CD52
ADNP
SCNN1A
FSTL5
PACS1
SYNCRIP
ADCY6
BRP44
SKIL
OTP
HAUS4
ZNF395
SEMA4C
LOX

TABLE 5A-continued (PGR_genes_up)

MPZ
DLG3
DLX2
FES
CA5B
KRT20
FGF17
OTX1
EEF1B2
NIPBL
KRTAP11-1
NCKAP5
NDUFS1
RAB30

TABLE 6A (AR_genes_up)

| | |
|---|---|
| TXNIP | FES |
| ZMYND8 | SPEG |
| SMOX | C6orf62 |
| C1orf51 | IP6K3 |
| PHF21A | C1orf43 |
| BCL6 | FAM162A |
| CD52 | ID2 |
| ADNP | ETV5 |
| PLAG1 | |
| SCNN1A | |
| RBM24 | |
| ADCY6 | |
| SGK1 | |
| TXNIP | |
| ZMYND8 | |
| SMOX | |
| TP53BP1 | |
| CD36 | |
| C1orf51 | |
| PHF21A | |

TABLE 6A-continued (AR_genes_up)

NAT14
CSAD
BCL6
ATP6V0A
KCNA5
DAGLA
ADNP
CEP57
SCNN1A
MXD4
RBM24
FOXJ3
FXYD1
UBE2Z
ZNF532
SIPA1
XK
PSME2
SLC43A1

TABLE 6B (AR_genes_dn)

PHC2
GOT2
DNAJB4
CDKN1A
MT2A
PIM2
TGIF1

TABLE 7A (PAX_genes_up)

| | |
|---|---|
| TRIB1 | MGAT3 |
| RERG | DCTN1 |
| CITED2 | NTN4 |
| DMD | MLLT10 |
| LMO3 | YWHAE |
| PCDH7 | MEX3B |
| FAM70A | NFE2L1 |
| MAB21L2 | IMPDH2 |
| NKX2-8 | PBX1 |
| SMC4 | ZBTB37 |
| OLFM2 | ACIN7 |
| AHCYL1 | ZNF532 |
| MAP1A | C2CD2L |
| ATG12 | HAUS4 |
| TFAP2B | MAP3K11 |
| ZMYND8 | SEMA6A |
| IGFBP5 | BCL6B |
| PPAP2B | SNX12 |
| C17orf80 | STAG2 |
| MNT | LRCH4 |
| FAM104A | TLN1 |
| HPCAL1 | FLVCR2 |
| MOV10 | |
| SIX5 | |
| JUB | |
| CDKN1C | |
| ARF3 | |
| PCF11 | |
| LMO3 | |
| THBS3 | |
| WASF2 | |
| MAB21L2 | |
| NEDD4L | |
| TGFB3 | |
| SLC41A1 | |
| GDPD3 | |
| C5orf13 | |

TABLE 7A-continued (PAX_genes_up)

ZNF503
PLCB1

TABLE 7B (PAX_genes_down)

PCBP4
PHF15
RHOBTB2
PHACTR3
RAPGEFL1
ZIC2

TABLE 8A (AHR_genes_up)

SGK1
PCDH17
WSB1
RUNX1
PHF21A
HES1
MBNL1
HPCAL1
MOV10
JUB
MOSPD2
JAG1
BRSK1
SOX4
MAGED2
C12orf57
TM2D2
VEZF1
MEX3B
KAZALD1
CAMK2D
SESN2
CNTNAP1
PABPC1
ZBTB8A
NAGLU
JAZF1
NIPBL
ADAM9
INSM1
HK2
TGFB1
CNNM1
TRIM23
EIF4A2

TABLE 8B (AHR_genes_dn)

SHC1
PAX6
EPB41L4B
SRRM2
PPRC1
OPA3

TABLE 9A (RUNX_genes_up)

SLC2A3
BATF
ADAMTS8
FOXD2
PHF21A
FRMD4A
MEIS2
ARHGEF2
ARF3
TACC2
PCF11
LMO3
SLC37A2
RCOR2
THBS3
RORC
SCNN1A
NUCB2
PACS1
RCC2
MOAP1
DNASE2B
ITGB7
BCAR3
ANK3
STAT2
ACIN1
DKFZp761E198
MAP3K11
DENND2D
SIRT1
S100A9

TABLE 9B (RUNX_genes_down)

LCOR
NOTCH2
LUZP1
PAX6
NSUN4
BMP
RILPL1
HOXC6
PCGF6
INPPL1
SLC37A4
RHOG
GPR137B
KRT73

TABLE 10B (ERBB2_genes_down)

SPAG4
FAM174B
SLC2A10
CREB3L2
TNFRSF21
PDE4B
P4HA2

TABLE 10B-continued (ERBB2_genes_down)

CXCR4
CYP1B1

TABLE 10A (ERBB2_genes_up)

| | |
|---|---|
| MSX2 | ZNF467 |
| KIAA0513 | APOBEC3B |
| HEY1 | |
| NDRG1 | |
| CRLF1 | |
| NNT | |
| CYP1A1 | |
| SOX9 | |
| CEACAM6 | |
| FAM46C | |
| FMO5 | |
| BCL3 | |
| VIPR1 | |
| GRAMD3 | |
| ATXN1 | |
| FGFR4 | |
| EDN1 | |
| BCL6 | |
| ATP6V0A4 | |
| LMO3 | |
| S100P | |
| LAMB2 | |
| CLMN | |
| KRT7 | |
| GBF1 | |
| ANKMY2 | |
| TPK1 | |
| MALL | |
| GDPD3 | |
| PACS1 | |
| PTGER4 | |
| SLC12A2 | |
| CAPN5 | |
| B3GALT4 | |
| SERHL2 | |
| SDCBP | |
| SERHL | |
| CA8 | |
| DNAJC4 | |

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method comprising:
   testing for the presence of a phosphorylated Ser294 (phospho-Ser294) progesterone receptor (PR) in a patient sample using immunohistochemistry (IHC) and/or immunofluorescence (IF); and
   administering a therapeutically effective amount of a PR antagonist to the patient.

2. The method of claim 1, wherein a therapeutically effective amount of a PR antagonist is administered to the patient only if phospho-Ser294 PR is detected.

3. The method of claim 1, wherein the patient has been diagnosed with a breast cancer.

4. The method of claim 1, wherein the PR antagonist blocks phosphorylation of Ser294 of the PR.

5. The method of claim 1, wherein the PR antagonist comprises at least one of onapristone, mifepristone, aglepristone, and WAY-348.

6. The method of claim 1, wherein testing for the presence of phospho-Ser294 PR comprises bringing the patient sample into contact with an anti-phospho-Ser294 PR antibody.

7. The method of claim 1, wherein testing for the presense of phospho-Ser294 PR comprises detecting the ability of a cell from the patient sample to form a secondary mammosphere.

8. The method of claim 1, wherein the patient sample comprises blood.

9. The method of claim 1, wherein the patient sample comprises a biopsy of a tumor clinically classified as PR-negative.

10. The method of claim 1, wherein the PR antagonist blocks phosphorylation of Ser294 of the PR in the presence of progesterone.

* * * * *